(12) United States Patent
Karig et al.

(10) Patent No.: US 9,096,551 B2
(45) Date of Patent: Aug. 4, 2015

(54) METHOD FOR PRODUCING 2-(TRIAZINYLCARBONYL) SULFONANILIDES

(75) Inventors: Gunter Karig, Hofheim am Taunus (DE); Mark James Ford, Schmitten (DE); Konrad Siegel, Düsseldorf (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 120 days.

(21) Appl. No.: 13/995,886

(22) PCT Filed: Dec. 19, 2011

(86) PCT No.: PCT/EP2011/073287
§ 371 (c)(1),
(2), (4) Date: Sep. 26, 2013

(87) PCT Pub. No.: WO2012/084857
PCT Pub. Date: Jun. 28, 2012

(65) Prior Publication Data
US 2014/0024828 A1    Jan. 23, 2014

Related U.S. Application Data

(60) Provisional application No. 61/425,349, filed on Dec. 21, 2010, provisional application No. 61/467,598, filed on Mar. 25, 2011.

(30) Foreign Application Priority Data

Dec. 21, 2010 (EP) ..................................... 10196205
Mar. 25, 2011 (EP) ..................................... 11159875
Nov. 15, 2011 (DE) ........................ 10 2011 086 382

(51) Int. Cl.
*C07D 251/00* (2006.01)
*C07D 251/20* (2006.01)
*C07D 403/04* (2006.01)

(52) U.S. Cl.
CPC ............ *C07D 251/20* (2013.01); *C07D 403/04* (2013.01)

(58) Field of Classification Search
USPC ........................................................ 544/219
See application file for complete search history.

(56) References Cited

U.S. PATENT DOCUMENTS

| 4,021,469 | A | 5/1977 | Weston |
| 7,482,308 | B2 | 1/2009 | Araki et al. |
| 7,829,703 | B2 | 11/2010 | Araki et al. |
| 8,008,484 | B2 | 8/2011 | Araki et al. |
| 2007/0197390 | A1 | 8/2007 | Araki et al. |
| 2007/0219199 | A1 | 9/2007 | Araki et al. |
| 2008/0312084 | A1 | 12/2008 | Araki et al. |
| 2009/0062536 | A1 | 3/2009 | Araki et al. |
| 2009/0305894 | A1 | 12/2009 | Araki et al. |
| 2010/0323896 | A1 | 12/2010 | Araki et al. |

FOREIGN PATENT DOCUMENTS

| JP | 2000044546 A | 2/2000 |
| WO | 9309099 A2 | 5/1993 |
| WO | 9641799 A1 | 12/1996 |
| WO | 2005096818 A1 | 10/2005 |
| WO | 2006008159 A1 | 1/2006 |
| WO | 2007031208 A2 | 3/2007 |

OTHER PUBLICATIONS

International Search Report for PCT/EP2011/073287 Mailed Jun. 5, 2012.

*Primary Examiner* — Jeffrey H Murray
*Assistant Examiner* — Oluwafemi Masha
(74) *Attorney, Agent, or Firm* — Miles & Stockbridge PC

(57) ABSTRACT

The present application relates to a process based on the oxidative ring opening of a compound with oxindole structure for preparation of substituted 2-(triazinylcarbonyl)sulfonanilides of the formula (1-1) proceeding from N-sulfonyl-substituted 3-triazinyloxindole of the formula (2-1), and to the 2-(triazinylcarbonyl)sulfonanilides of the formula (1-1) thus prepared, and to the use thereof as intermediates for the synthesis of fine chemicals and of active ingredients in the agricultural sector.

The invention also relates to a multistage process for preparation of N-alkyl-N-[2-(1,3,5-triazin-2-ylcarbonyl)phenyl] alkanesulfonamides of the formula (4-1), proceeding from a 3-(alkylsulfanyl)-1,3-dihydro-2H-indol-2-one of the formula (7-1), wherein the multistage process also comprises, as a component step, the oxidative ring opening mentioned, and to the 2-(triazinylcarbonyl)sulfonanilides of the formula (1-1) which are obtained by the oxidative ring opening and are used as intermediates in the multistage process.

15 Claims, No Drawings

METHOD FOR PRODUCING 2-(TRIAZINYLCARBONYL) SULFONANILIDES

CROSS REFERENCE TO RELATED APPLICATIONS

This application is a §371 National Stage Application of PCT/EP2011/073287, filed Dec. 19, 2011, which claims priority to European Application No. 10196205.8, filed Dec. 21, 2010; U.S. Provisional Application No. 61/425,349, filed Dec. 21, 2010; European Application No. 11159875.1, filed Mar. 25, 2011; U.S. Provisional Application No. 61/467,598, filed Mar. 25, 2011; and German Application No. 10 2011 086 382.6, filed Nov. 15, 2011.

BACKGROUND OF THE INVENTION

1. Field of the Invention

The present application relates to a process based on the oxidative ring opening of a compound with oxindole structure for preparation of substituted 2-(triazinylcarbonyl)sulfonanilides of the formula (1-1) proceeding from N-sulfonyl-substituted 3-triazinyloxindoles of the formula (2-1), and to the 2-(triazinylcarbonyl)sulfonanilides of the formula (1-1) thus prepared, and to the use thereof as intermediates for the synthesis of fine chemicals and of active ingredients in the agricultural sector.

DESCRIPTION OF RELATED ART

The invention also relates to a multistage process for preparation of N-alkyl-N-[2-(1,3,5-triazin-2-ylcarbonyl)phenyl]alkanesulfonamides of the formula (4-1), proceeding from a 3-(alkylsulfanyl)-1,3-dihydro-2H-indol-2-one of the formula (7-1), wherein the multistage process also comprises the oxidative ring opening mentioned as a component step. The intermediates used in the multistage process, as well as the 2-(triazinylcarbonyl)sulfonanilides of the formula (1-1), are also triazinyl-substituted oxindoles of the formula (5-1) and N-sulfonyl-substituted 3-triazinyloxindoles of the formula (2-1), the subject-matter of the present invention likewise including triazinyl-substituted oxindoles of the formula (5-1) and N-sulfonyl-substituted 3-triazinyloxindoles of the formula (2-1), and the use thereof as intermediates for the synthesis of fine chemicals and of active ingredients in the agricultural sector.

It is known that sulfonanilides can have herbicidal activity (WO 93/09099, WO 96/41799, WO 2005/096818, WO 2007/031208 and US 2009/0062536) or fungicidal activity (WO 2006/008159).

The sulfonanilides with herbicidal or fungicidal action disclosed in the prior art also comprise the 2-(triazinylcarbonyl)sulfonanilides as a subgroup.

According to the prior art, 2-(triazinylcarbonyl)sulfonanilides can be prepared by various routes. However, the processes known from the prior art for preparation of 2-(triazinylcarbonyl)sulfonanilides do not have the aim of performance of the reaction on the industrial scale.

The document US 2009/0062536 describes the preparation of a substituted 2-(triazinylcarbonyl)sulfonanilide A1, as summarized in scheme 1.

Scheme 1: Preparation of a 2-(triazinylcarbonyl)sulfonanilide (U.S. 2009/0062536)

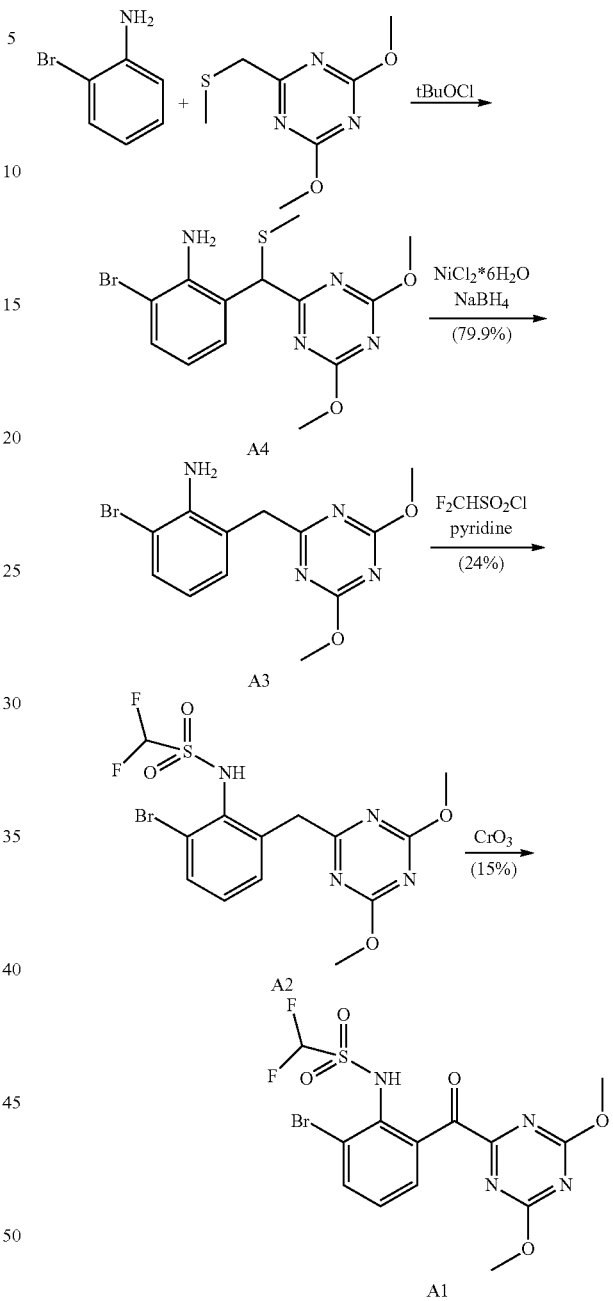

In the process according to scheme 1, the substituted 2-[(methylsulfanyl)(1,3,5-triazin-2-yl)methyl]aniline A4 is reduced with nickel chloride hexahydrate and sodium borohydride to give a 2-(1,3,5-triazin-2-ylmethyl)aniline A3 (synthesis example 13 in US 2009/0062536). This process is sulfonylated to give an N-[2-(1,3,5-triazin-2-ylmethyl)phenyl]alkanesulfonamide A2 (synthesis example 15 in US 2009/0062536). This is followed by oxidation with four equivalents of chromium(VI) oxide to give the desired product A1 (synthesis example 17 in US 2009/0062536). The yield of the oxidation disclosed in US 2009/0062536 is 15%.

The use of the process according to scheme 1 on the industrial scale has the disadvantage that the carcinogenic reagents chromium(VI) oxide and nickel chloride hexahydrate have to be used in excess, and still only small yields are achieved.

In addition to the disadvantages mentioned in the process regime of the preparation route described in scheme 1, it should be emphasized that the preparation of the 2-[(methylsulfanyl)(1,3,5-triazin-2-yl)methyl]aniline A4 used as the reactant in scheme 1 is also costly and inconvenient. The preparation of reactant A4 is likewise described in US 2009/0062536 (synthesis example 7 in US 2009/0062536). For this purpose, a substituted aniline is reacted with tert-butyl hypochlorite and 2-[(methylsulfanyl)methyl]-1,3,5-triazine.

However, the industrial use of this process has the disadvantage that it is necessary to use the explosive tert-butyl hypochlorite as a reagent.

Moreover, the 2-[(methylsulfanyl)methyl]-1,3,5-triazine used is a synthesis unit whose preparation proceeds over several stages and whose use is therefore disadvantageous for industrial applications.

The preparation route shown in scheme 1, more particularly the oxidation of N-[2-(1,3,5-triazin-2-ylmethyl)phenyl]alkanesulfonamides (see compound A2 in scheme 1), is also described by similar synthesis examples in further documents (WO 2007/031208, WO2006/008159 and WO2005/096818A1).

The process disclosed in WO 2007/031208 is shown in scheme 2. This is an alternative process to the process shown in scheme 1 for preparation of substituted 2-(triazinylcarbonyl)sulfonanilides.

Scheme 2:
Preparation of a 2-(triazinylcarbonyl)sulfonanilide (WO 2007/031208)

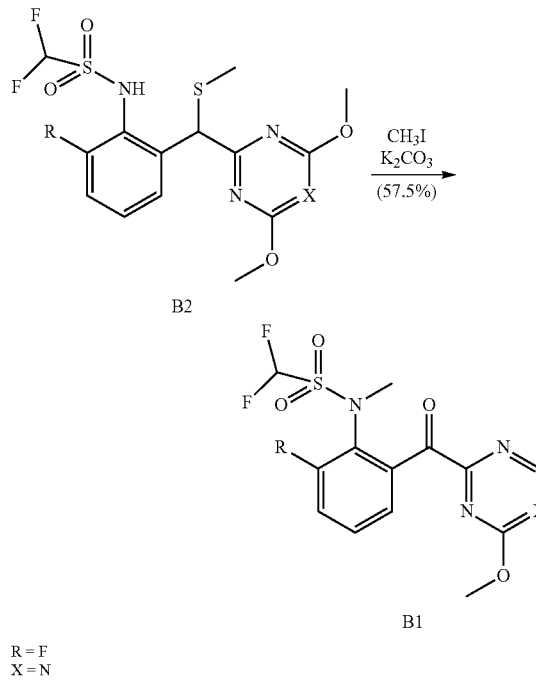

R = F
X = N

According to WO 2007/031208, an N-{2-[(4,6-dimethoxy-1,3,5-triazin-2-yl)(methylsulfanyl)methyl]phenyl}methanesulfonamide B2 is stirred with potassium carbonate and iodomethane in a solvent for 48 hours, and then the desired product B1 is isolated (reference example 2 in WO 2007/031208).

However, the yield is only 57.5%.

Moreover, the use of the process shown in scheme 2 on the industrial scale has the disadvantage that the oxidation of B2 to B1 is always accompanied by an alkylation on the nitrogen, and therefore it is not possible to directly obtain a compound not alkylated on the nitrogen by this route. The methyl iodide used as the alkylating agent is also problematic from a technical point of view due to its high vapor pressure and toxicity. Moreover, the long reaction time is also disadvantageous.

The practicability of the preparation of the N-{2-[(4,6-dimethoxy-1,3,5-triazin-2-yl)(methylsulfanyl)methyl]phenyl}methanesulfonamide B2 used as the reactant in scheme 2 is shown in WO 2007/031208 not using the example of the triazine compound (X=N), but only using the example of a pyrimidine compound (X=CH), as summarized in scheme 3.

Scheme 3: Preparation of an N-{2-[(4,6-dimethoxypyrimidin-2-yl)(methylsulfanyl)methyl]phenyl}methanesulfonamide C2 (WO 2007/031208)

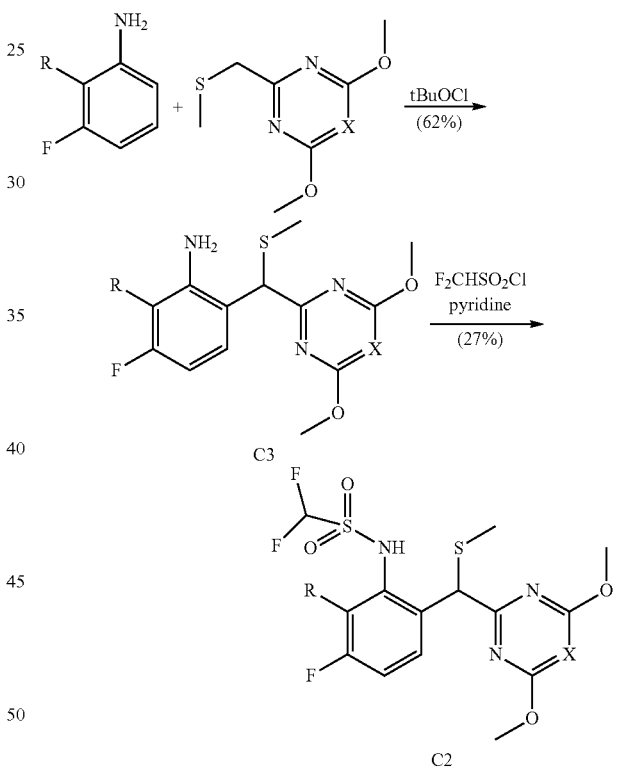

R = OCH₃
X = CH

In this case, a substituted aniline is reacted with tert-butyl hypochlorite and 2-[(methylsulfanyl)methyl]pyrimidine, and a 2-[(4,6-dimethoxypyrimidin-2-yl)(methylsulfanyl)methyl]aniline C3 is obtained as an intermediate (synthesis example 10 in WO 2007/031208). This compound is sulfonylated to give an N-{2-[(4,6-dimethoxypyrimidin-2-yl)(methylsulfanyl)methyl]phenyl}methanesulfonamide C2 (synthesis example 9 in WO 2007/031208). The yield of the sulfonylation is only 27%.

Tables 5 and 6 of document WO 2007/031208 also list examples of N-{2-[(4,6-dimethoxy-1,3,5-triazin-2-yl)(methylsulfanyl)methyl]phenyl}methanesulfonamides B2 or 2-[(4,6-dimethoxy-1,3,5-triazin-2-yl)(methylsulfanyl)methyl]anilines which have been prepared in a similar manner to C2 and C3.

However, the industrial application of the process shown in scheme 3 has the disadvantage that it is necessary to use the explosive tert-butyl hypochlorite (BuOCl) as a reagent, and the yield in the sulfonylation reaction is low. Furthermore, the 2-[(methylsulfanyl)methyl]pyrimidine used is a synthesis unit whose preparation likewise proceeds over several stages and is therefore disadvantageous for industrial application.

In another previously known process for preparation of substituted 2-(triazinylcarbonyl)sulfonanilides, the oxidation to give the desired product is performed with hydrogen peroxide. For instance, the document US 2009/0062536 already cited describes the preparation of N-{2-[(4,6-dimethoxypyrimidin-2-yl)carbonyl]phenyl}alkanesulfonamides D1 from N-{2-[(4,6-dimethoxypyrimidin-2-yl)(methylsulfanyl)methyl]phenyl}alkanesulfonamides D2 by oxidation with hydrogen peroxide in glacial acetic acid (see synthesis examples 3, 4 in US 2009/0062536), as summarized in scheme 4.

Scheme 4: Preparation of N-{2-[(4,6-dimethoxypyrimidin-2-yl)carbonyl]phenyl}alkanesulfonamides D1 by oxidation with hydrogen peroxide (U.S. 2009/0062536)

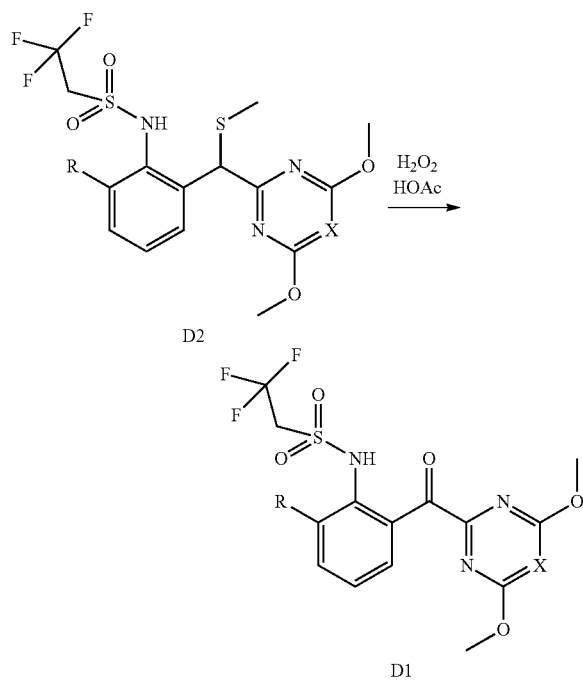

R = Br, I
X = CH

Tables 2 and 3 of document US 2009/0062536 also list examples of N-{2-[(4,6-dimethoxy-1,3,5-triazin-2-yl)carbonyl]phenyl}-N-alkylmethanesulfonamides E1 (i.e. X=N) which have been prepared in a similar manner to D1 and always contain an alkyl radical on the nitrogen (see scheme 5 below).

Scheme 5: Preparation of N-{2-[(4,6-dimethoxy-1,3,5-triazin-2-yl)carbonyl]phenyl}-N-alkyl-1,1-difluoromethanesulfonamides E1 (U.S. 2009/0062536)

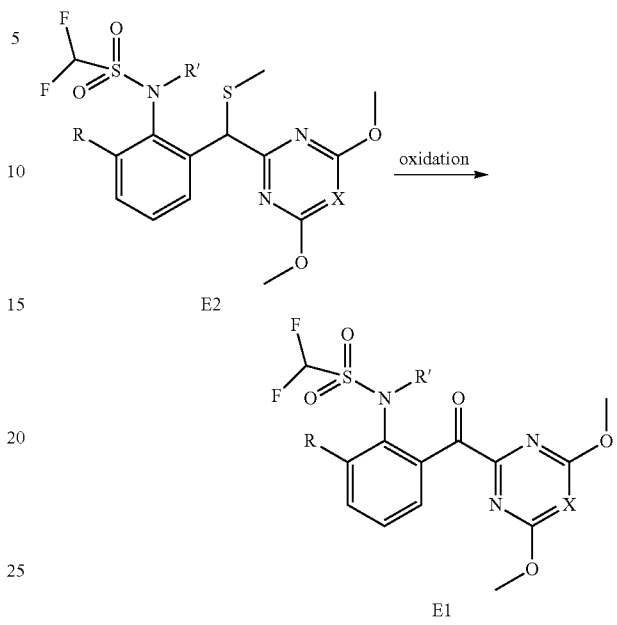

R = Br, I
X = N
R' = alkyl

In this process, it is necessary to use N-{2-[(4,6-dimethoxy-1,3,5-triazin-2-yl)(methylsulfanyl)methyl]phenyl}methanesulfonamides E2 as reactants, the preparation of which on the industrial scale has the disadvantages described above. The oxidation reaction in this process takes place on the sulfur at first. Under the acidic reaction conditions, the hydrolysis then proceeds to give the ketone. The presence of an oxidizable sulfur substituent is therefore a necessary prerequisite for the process.

However, it is not evident from document US 2009/0062536 whether 2-(triazinylcarbonyl)sulfonanilides which have not been alkylated on the nitrogen can also be prepared by this process. It is also unclear whether the oxidation reaction to give these compounds is performable with hydrogen peroxide, since chromic anhydride was used as the oxidizing agent in the use examples executed in US 2009/0062536, in which N-{2-[(4,6-dimethoxy-1,3,5-triazin-2-yl)carbonyl]phenyl}-N-alkylmethanesulfonamides were prepared (see synthesis examples 17, 18 in US 2009/0062536).

WO 2007/031208 also mentions the possibility of preparation of N-{2-[(4,6-dimethoxypyrimidin-2-yl)carbonyl]phenyl}alkanesulfonamides by oxidation with hydrogen peroxide. In the use examples executed for preparation of N-{2-[(4,6-dimethoxy-1,3,5-triazin-2-yl)carbonyl]phenyl}methanesulfonamides, the oxidation is, however, performed exclusively with chromium(VI)oxide.

Thus, the aforementioned processes known from the prior art have the disadvantage that, for the reasons mentioned above, they are only of limited suitability for preparation of 2-(triazinylcarbonyl)sulfonanilides on the industrial scale due to the disadvantages mentioned.

In the search for an industrially usable process for preparation of 2-(triazinylcarbonyl)sulfonanilides, it was first recognized in the context of the present invention that (N-[2-(1,3,5-triazin-2-ylcarbonyl)phenyl]alkanesulfonamides could possibly be prepared from N-sulfonyl-substituted 3-triaziny-loxindoles by the oxidative ring opening shown in scheme 6a.

Scheme 6a: Synthesis of 2-(triazinylcarbonyl)sulfonanilides from N-sulfonyl-substituted 3-triazinyloxindoles

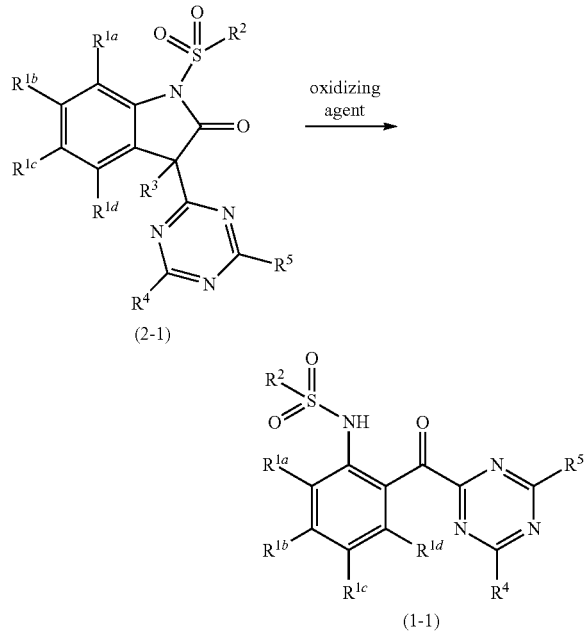

In terms of the general principle, the oxidative ring opening of 3-phenyl-1,3-dihydro-2H-indol-2-ones to (2-aminophenyl)(phenyl)methanones is known. It is likewise known that the oxidation can be effected with oxygen or with hydrogen peroxide.

For instance, the oxidation of 1-methyl-3-phenyl-1,3-dihydro-2H-indol-2-one with oxygen in the presence of cobalt catalysts is disclosed in the scientific publication Heterocycles, 1982, 2139, the main product of the oxidation being the dimer of the reactant, namely 2-methylaminobenzophenone. Another product formed is a (2-aminophenyl)(phenyl)methanone, but in only a small yield, namely at 2% to 6%.

Document U.S. Pat. No. 4,021,469 discloses the oxidation of 3-phenyl-1,3-dihydro-2H-indol-2-ones with oxygen in the presence of sodium methoxide in methanol. The methyl carbamates are formed at first, and are then cleaved in a second reaction step after addition of potassium hydroxide or water, as a result of which sodium hydroxide forms, by heating under reflux for several hours to give (2-aminophenyl)(phenyl)methanone. However, these conditions (see example 4 in U.S. Pat. No. 4,021,469) are unsuitable for the conversion of 3-(1,3,5-triazin-2-yl)-1,3-dihydro-2H-indol-2-ones, since the triazine ring would be cleaved hydrolytically.

The oxidation of 3-hydroxy-3-phenylindolin-2-ones by means of hydrogen peroxide is described in J. Chemical Soc., 1959, 2366. The reactants used are prepared by addition of the phenyl Grignard compound or phenyllithium onto the corresponding isatins.

However, the preparation of the corresponding 3-hydroxy-3-(1,3,5-triazin-2-yl)-1,3-dihydro-2H-indol-2-ones is industrially unviable because preparation and conversion of the triazinyl Grignard compounds required as reactants, or of the triazinyllithium compounds, are difficult under industrial conditions.

The conditions described in J. Chemical Soc., 1959, 2366 for oxidation, which is performed in the presence of a large excess of aqueous sodium hydroxide solution at 90° C. to 95° C., are unsuitable for the conversion of 3-(1,3,5-triazin-2-yl)-1,3-dihydro-2H-indol-2-ones due to the temperature, since the triazine ring would be cleaved hydrolytically. The yield is 60%.

However, it is not clear from these examples whether, under the conditions described for preparation of (2-aminophenyl)(phenyl)methanones, oxidative ring opening of 1,3-dihydro-2H-indol-2-ones having a 6-membered heterocyclic ring, especially a triazine, in the 3 position in place of the phenyl ring would also be possible to give the corresponding (2-aminophenyl)carbonyltriazines. It is also unclear whether the reaction is performable in an economically viable manner on the industrial scale too.

SUMMARY

Against this background it is an object of the invention to provide an alternative process for preparing 2-(triazinylcarbonyl)sulfonanilides on the industrial scale, i.e. to provide a process for industrial production of 2-(triazinylcarbonyl)sulfonanilides with a very simple process regime and maximum yields.

The object is achieved by a process for preparing 2-(triazinylcarbonyl)sulfonanilides of the formula (1-1)

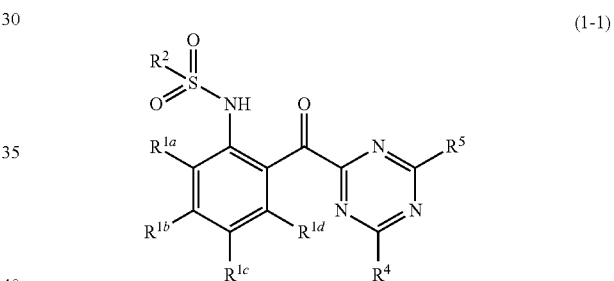

in which
$R^{1a}$ to $R^{1d}$ are each independently selected from the group consisting of hydrogen, fluorine, chlorine, bromine, iodine and from
($C_1$-$C_6$)-alkyl where the alkyl radical is branched or unbranched and is unsubstituted or substituted by one or more substituents selected from the group consisting of fluorine, chlorine, ($C_1$-$C_4$)-alkoxy and ($C_3$-$C_7$)-cycloalkyl,
($C_3$-$C_7$)-cycloalkyl where the cycloalkyl radical is unsubstituted or substituted by one or more substituents selected from the group consisting of fluorine, chlorine, ($C_1$-$C_4$)-alkyl and ($C_3$-$C_7$)-cycloalkyl and ($C_1$-$C_4$)-alkoxy,
($C_1$-$C_6$)-alkoxy where the alkoxy radical is branched or unbranched and is unsubstituted or substituted by one or more substituents selected from the group consisting of fluorine, chlorine, ($C_1$-$C_4$)-alkoxy and ($C_3$-$C_7$)-cycloalkyl,
($C_3$-$C_7$)-cycloalkoxy where the cycloalkoxy radical is unsubstituted or substituted by one or more substituents selected from the group consisting of fluorine, chlorine, ($C_1$-$C_4$)-alkyl and ($C_1$-$C_4$)-alkoxy,
($C_1$-$C_6$)-alkylthio where the alkylthio radical is branched or unbranched and is unsubstituted or substituted by one or more substituents selected from the group consisting of fluorine, chlorine, ($C_1$-$C_4$)-alkyl and ($C_1$-$C_4$)-alkoxy,
($C_3$-$C_7$)-cycloalkylthio where the cycloalkylthio radical is unsubstituted or substituted by one or more substituents selected from the group consisting of fluorine, chlorine, $(C_1-C_4)$-alkyl and $(C_1-C_4)$-alkoxy, and phenyl or 1-naphthyl or 2-naphthyl or a five- or six-membered heteroaromatic ring having 1 to 2 heteroatoms, where the heteroatoms are each selected independently from the group consisting of O and N, and where the aryl or heteroaryl radical is unsubstituted or substituted by one or more substituents selected from the group consisting of fluorine, chlorine, bromine, iodine, $(C_1-C_4)$-alkyl, $(C_1-C_4)$-alkoxy and $(C_3-C_7)$-cycloalkyl and $(C_1-C_4)$-alkylthio, and $R^2$ is $(C_1-C_6)$-alkyl where the alkyl radical is unsubstituted or fully or partly substituted by fluorine, or $(C_3-C_7)$-cycloalkyl where the cycloalkyl radical is unsubstituted or fully or partly substituted by fluorine, and $R^4$ and $R^5$ are each hydrogen, $(C_1-C_6)$-alkyl where the alkyl radical is unsubstituted or substituted by one or more substituents selected from fluorine, chlorine, $(C_1-C_4)$-alkoxy and $(C_3-C_7)$-cycloalkyl, or $(C_1-C_6)$-alkoxy where the alkoxy radical is branched or unbranched and is unsubstituted or substituted by one or more substituents selected from the group consisting of fluorine, chlorine, $(C_1-C_4)$-alkoxy and $(C_3-C_7)$-cycloalkyl, which comprises using as the reactant an N-sulfonyl-substituted 3-triaziny-loxindole of the formula (2-1)

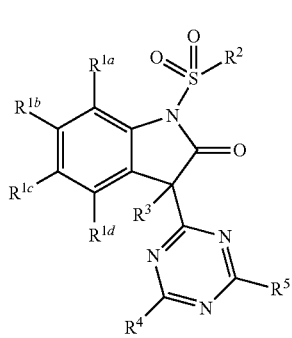

(2-1)

in which
$R^{1a}$ to $R^{1d}$ and $R^2$, $R^4$ and $R^5$ are each as defined in formula (1-1), and
$R^3$ is hydrogen
and
converting the reactant of the general formula (2-1) initially charged in a solvent in the presence
of a base and
of an oxidizing agent.

DETAILED DESCRIPTION OF A PREFERRED EMBODIMENT

The core idea of the process according to the invention for preparation of compounds of the formula (1-1) relates to the selection of an oxindole, especially of an N-sulfonyl-substituted 3-triazinyloxindole of the formula (2-1), as a reactant and in the conversion thereof by oxidative ring opening.

The reactant initially charged in a suitable solvent is first deprotonated with a suitable base. After addition of the oxidizing agent, the desired oxidative ring opening of compounds of the formula (2-1) takes place to give compounds of the formula (1-1).

The preparation of the N-sulfonyl-substituted 3-triaziny-loxindoles of the formula (2-1) used as reactants on the industrial scale is described in patent application EP 111598751.

Particular preference is given to the preparation of 2-(triazinylcarbonyl)sulfonanilides of the formula (1-1) where $R^{1a}$ to $R^{1d}$ are each independently selected from the group consisting of hydrogen, fluorine, chlorine, bromine, iodine and from $(C_1-C_6)$-alkyl where the alkyl radical is branched or unbranched and is unsubstituted or substituted by one or more substituents selected from the group consisting of fluorine, chlorine, $(C_1-C_4)$-alkoxy or $(C_3-C_7)$-cycloalkyl, $(C_3-C_7)$-cycloalkyl where the cycloalkyl radical is unsubstituted or substituted by one or more substituents selected from the group consisting of fluorine, chlorine, $(C_1-C_4)$-alkyl or $(C_3-C_7)$-cycloalkyl or $(C_1-C_4)$-alkoxy, $(C_1-C_6)$-alkoxy where the alkoxy radical is branched or unbranched and is unsubstituted or substituted by one or more substituents selected from the group consisting of fluorine, chlorine, $(C_1-C_4)$-alkoxy or $(C_3-C_7)$-cycloalkyl, $(C_3-C_7)$-cycloalkoxy where the cycloalkoxy radical is unsubstituted or substituted by one or more substituents selected from the group consisting of fluorine, chlorine, $(C_1-C_4)$-alkyl or $(C_1-C_4)$-alkoxy, and $R^2$ is $(C_1-C_6)$-alkyl where the alkyl radical is fully or partly substituted by fluorine, and $R^3$ is as defined in claim 1, and $R^4$ and $R^5$ are each independently $(C_1-C_6)$-alkoxy where the alkoxy radical is branched or unbranched and is unsubstituted or substituted by one or more substituents selected from the group consisting of fluorine, chlorine, $(C_1-C_4)$-alkoxy or $(C_3-C_7)$-cycloalkyl.

Very particular preference is given to the preparation of 2-(triazinylcarbonyl)sulfonanilides of the formula (1-1), where $R^{1a}$ to $R^{1d}$ are each independently selected from the group consisting of hydrogen, fluorine, chlorine, methoxy and $R^2$ is difluoromethyl and $R^3$ is hydrogen, and $R^4$ and $R^5$ each methoxy.

With regard to the inventive compounds, the designations used above and below will be explained collectively. These are familiar to the person skilled in the art and have, more particularly, the definitions explained hereinafter:

The term "halogen" means, for example, fluorine, chlorine, bromine or iodine. If the term is used for a radical, "halogen" means, for example, a fluorine, chlorine, bromine or iodine atom.

Alkyl is a straight-chain or branched open-chain saturated hydrocarbyl radical.

The expression "$(C_1-C_4)$alkyl" is a brief notation for alkyl having one to four carbon atoms, according to the range stated for carbon atoms, which means that it includes the methyl, ethyl, 1-propyl, 2-propyl, 1-butyl, 2-butyl, 2-methylpropyl or tert-butyl radicals. General alkyl radicals having a greater specified range of carbon atoms, e.g. "$(C_1-C_6)$alkyl", correspondingly also include straight-chain or branched alkyl radicals having a greater number of carbon atoms, i.e. according to the example also the alkyl radicals having 5 and 6 carbon atoms.

Cycloalkyl is a carbocyclic saturated ring system having preferably 3-8 ring carbon atoms, e.g. cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene.

In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl(norbornyl), adamantan-1-yl and adamantan-2-yl.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl.

Aryl is a mono-, bi- or polycyclic aromatic system having preferably 6 to 14 and especially 6 to 10 ring carbon atoms, for example phenyl, naphthyl, anthryl, phenanthrenyl, and the like, preferably phenyl.

The term "optionally substituted aryl" also includes polycyclic systems, such as tetrahydronaphthyl, indenyl, indanyl, fluorenyl, biphenylyl, where the bonding site is on the aromatic system.

In systematic terms, aryl is generally also encompassed by the term "optionally substituted phenyl".

Alkoxy is an alkyl radical bonded via an oxygen atom, alkenyloxy is an alkenyl radical bonded via an oxygen atom, alkynyloxy is an alkynyl radical bonded via an oxygen atom, cycloalkyloxy is a cycloalkyl radical bonded via an oxygen atom, and cycloalkenyloxy is a cycloalkenyl radical bonded via an oxygen atom.

Alkylthio is an alkyl radical bonded via a sulfur atom, alkenylthio is an alkenyl radical bonded via a sulfur atom, alkynylthio is an alkynyl radical bonded via a sulfur atom, cycloalkylthio is a cycloalkyl radical bonded via a sulfur atom, and cycloalkenylthio is a cycloalkenyl radical bonded via a sulfur atom.

Haloalkyl, -alkenyl and -alkynyl are, respectively, alkyl, alkenyl and alkynyl partly or fully substituted by identical or different halogen atoms, for example monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$; haloalkoxy is, for example, $OCF_3$, $OCHF_2$, $OCH_2F$, $OCF_2CF_3$, $OCH_2CF_3$ and $OCH_2CH_2Cl$; the same applies to haloalkenyl and other halogen-substituted radicals.

The definition "substituted by one or more radicals" means, unless defined otherwise, independently one or more identical or different radicals, where two or more radicals on one cycle as a base structure may form one or more rings.

Substituted radicals, such as a substituted alkyl, cycloalkyl, cycloalkenyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl or a group equivalent to the carboxyl group, isocyano, azido, alkoxycarbonyl, alkylcarbonyl, formyl, carbamoyl, mono- and dialkylaminocarbonyl, substituted amino, such as acylamino, mono- and dialkylamino, trialkylsilyl and optionally substituted cycloalkyl, optionally substituted aryl, optionally substituted heterocyclyl, where each of the latter cyclic groups may also be bonded via heteroatoms or divalent functional groups as in the alkyl radicals mentioned, and alkylsulfinyl, including both erastiomers of the alkylsulfinyl group, alkylsulfonyl, alkylphosphinyl, alkylphosphonyl and, in the case of cyclic radicals (="cyclic base structures"), also alkyl, haloalkyl, alkylthioalkyl, alkoxyalkyl, optionally substituted mono- and dialkylaminoalkyl, and hydroxyalkyl.

The term "substituted radicals", such as substituted alkyl etc., includes, as substituents, as well as the saturated hydrocarbonaceous radicals mentioned, corresponding unsaturated aliphatic and aromatic radicals, such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and dialkenylaminocarbonyl, mono- and dialkynylaminocarbonyl, mono- and dialkenylamino, mono- and dialkynylamino, trialkenylsilyl, trialkynylsilyl, optionally substituted cycloalkenyl, optionally substituted cycloalkynyl, phenyl, phenoxy etc. In the case of substituted cyclic radicals with aliphatic components in the ring, cyclic systems with those substituents which are bonded by a double bond to the ring are also included, for example by alkylidene group such as methylidene or ethylidene, or an oxo group, imino group or substituted imino group.

Each of the unsubstituted or substituted radicals may be branched and unbranched. For example, a radical designated "$C_4$-alkyl" comprises, as well as the unbranched butyl radical, all other $C_4$ isomers, including tert-butyl.

When two or more radicals form one or more rings, these may be carbocyclic, heterocyclic, saturated, partly saturated, unsaturated, for example also aromatic and optionally further-substituted. The fused rings are preferably 5- or 6-membered rings, particular preference being given to benzofused cycles.

In a preferred embodiment of the process, the use of a heavy metal catalyst which has at least one heavy metal or the salt of a heavy metal as constituent is envisaged for particularly efficient performance of the oxidative ring opening on the compounds of the formula (2-1) selected as the reactant. Suitable heavy metals are vanadium, chromium, manganese, iron, cobalt, nickel, copper, zinc, tin, antimony, bismuth, silver, gold, tungsten, ruthenium and/or osmium.

Advantageously, the effect of the heavy metal catalyst is to reduce the level of unwanted by-products and thus to enable the product yield of the reaction to be increased.

For instance, in the oxidation of the N-sulfonyl-substituted 3-triazinyloxindoles of the formula (2-1) shown in scheme 6b below with aqueous solutions of hydrogen peroxide, it was found that, if no catalyst is used, as well as the ketone of the formula (1-1) desired as the product, a large proportion of the alcohol of the formula (3-1) is disadvantageously also formed as a by-product.

Scheme 6b:
Formation of ketone (1-1) and alcohol (3-1) in the oxidation of N-sulfonyl-substituted 3-triazinyloxindoles (2-1) without catalyst

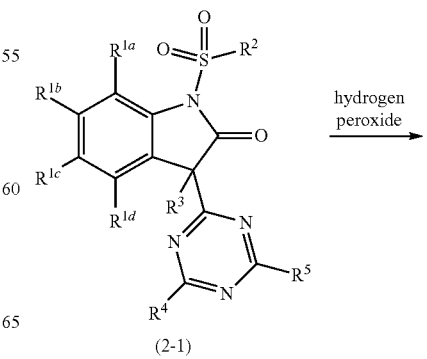

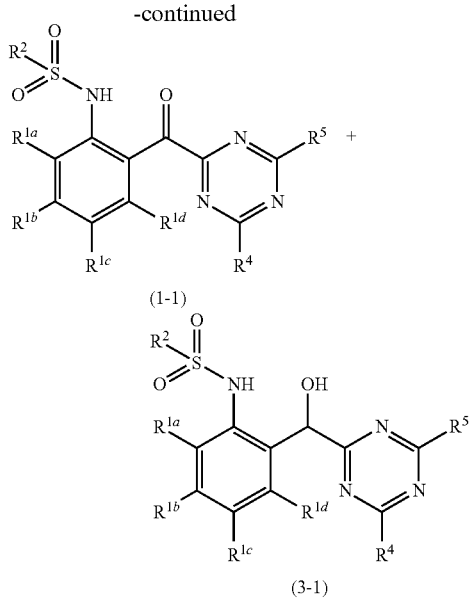

(1-1)

(3-1)

The formation of alcohols of the formula (3-1), which do not react further to give the ketone of the formula (1-1) under the reaction conditions, leads to yield losses and is therefore disadvantageous.

It is not clear from the prior art cited above regarding oxidative ring opening of 3-phenyl-1,3-dihydro-2H-indol-2-ones that the oxidative ring opening of N-sulfonyl-substituted 3-triazinyloxindoles (2-1) by hydrogen peroxide does in fact lead to partial formation of alcohols of the formula (3-1) (see scheme 6b). Nor can any technical teaching regarding the avoidance of disadvantageous alcohol formation be found in the prior art.

For evidence of unwanted by-product formation, in the form of comparative synthesis example 1 variant C (see EXAMPLES), the oxidation of an N-sulfonyl-substituted 3-triazinyloxindole with an aqueous solution of hydrogen peroxide was performed without addition of a catalyst. The product obtained is a mixture which, according to HPLC analysis (area percent), consists to an extent of approx. 13% of the ketone and to an extent of approx. 76% of the alcohol. This ratio of ketone to alcohol was also confirmed by NMR.

It has now been found that, interestingly, the formation of alcohols of the formula (3-1) can be substantially or almost completely suppressed when the oxidation is performed with hydrogen peroxide in the presence of heavy metal salts, especially in the presence of iron salts.

Advantageously, the process allows the preparation of 2-(triazinylcarbonyl)sulfonanilides on the industrial scale with a very simple process regime, and the achievement of high yields of the desired ketone compound by the controlled avoidance of unwanted side reactions, which results in the formulation of unwanted alcohol compounds instead of the desired ketones.

In principle, an oxidative ring opening can be brought about by a multitude of oxidizing agents. In the context of the present invention, i.e. in the oxidative ring opening of oxindoles, the use of the oxidizing agent in conjunction with a catalyst has been found to be particularly advantageous.

The preferred oxidizing agent for the present invention is hydrogen peroxide in conjunction with a catalyst which has at least one heavy metal or the salt of a heavy metal as a constituent. Very particular preference is given to the use of an aqueous hydrogen peroxide solution in conjunction with a catalyst which has at least one heavy metal or the salt of a heavy metal as a constituent.

A further preferred oxidizing agent is potassium permanganate. This can be used alone or in conjunction with a catalyst which has at least one heavy metal or the salt of a heavy metal as a constituent.

The catalysts or catalyst systems used are preferably the heavy metal salts, heavy metal powders specified hereinafter, namely iron salts such as iron(II) sulfate, iron chloride, and
iron powder, and
copper salts such as copper(II) sulfate, copper(II) chloride, and
copper powder, and
mixtures of at least two of the aforementioned catalysts.

In order to increase the stability of the metal catalyst, one or more complexing substances can be added to the metal powder or the metal salt in each case, for example pyridine-2-carboxylic acid. Preference is given to mixtures of iron salts with complexing compounds, for example pyridine-2-carboxylic acid, and
mixtures of copper salts with complexing compounds, for example pyridine-2-carboxylic acid, or
mixtures of at least two of the aforementioned catalyst systems.

Particularly preferred iron salts are iron(II) sulfate or iron chloride, or mixtures of the two salts. Very particularly preferred copper salts are copper(II) sulfate or copper(II) chloride, or mixtures of the two salts.

A particularly preferred complexing compound is pyridine-2-carboxylic acid.

A most preferred catalyst system is a mixture consisting of iron(II) sulfate and pyridine-2-carboxylic acid.

With regard to this most preferred embodiment, reference is made by way of example to synthesis example 1 variant A, in which the oxidation of an N-sulfonyl-substituted 3-triazinyloxindole with aqueous solution of hydrogen peroxide is performed with addition of iron sulfate and pyridine-2-carboxylic acid as a catalyst system. The N-sulfonyl-substituted 3-triazinyloxindole used as the reactant is identical to the reactant used in synthesis example 1 variant C. The ketone corresponding to the formula (1-1) is obtained in a yield of 90%. No alcohol of the formula (3-1) as an unwanted by-product could be detected.

The solvents used are preferably organic solvents which are entirely or partly water-miscible. Organic solvents which are entirely or partly water-miscible are nitriles, especially acetonitrile, or
alcohols, especially 2-propanol, or
ketones, especially acetone.

The organic solvents mentioned are preferably used in a mixture with water.

Particular preference is given to the performance of the process with a mixture of acetonitrile and water as a solvent, or with a mixture of 2-propanol and water.

Very particular preference is given to the performance of the process with a solvent mixture composed of acetonitrile and water, in which the ratio of acetonitrile and water is in the range of 2:1 to 1:2.

If hydrogen peroxide is used as the oxidizing agent, the formation of acetone peroxides has to be expected when acetone is used as the solvent. The formation of acetone peroxide is disadvantageous for technical reasons. However, the disadvantage mentioned need not necessarily apply to all acetones usable as solvents.

The process is performed in the presence of a base. The base brings about complete or partial deprotonation of the N-sulfonyl-substituted 3-triazinyloxindoles used as the reactant. Because the reactants after the deprotonation are present in the more reactive enolate form, the use of bases bring about a faster reaction overall.

Preference is given to using the following bases:
potassium carbonate, sodium carbonate or cesium carbonate, and
potassium hydrogencarbonate or sodium hydrogencarbonate, and
lithium hydroxide, sodium hydroxide, potassium hydroxide or barium hydroxide, and
potassium phosphate ($K_3PO_4$), potassium hydrogenphosphate ($K_2HPO_4$) or sodium phosphate.

It is within the scope of the invention that the bases used are also ammonium hydroxides of the formula $N(R^{10})_4OH$ with tetrasubstitution on the nitrogen, in which the $R^{10}$ radicals are each independently selected from the group consisting of $(C_1-C_6)$-alkyl, where the alkyl radical is branched or unbranched, and benzyl.

Particularly preferred bases are potassium carbonate or potassium hydrogencarbonate, each of which is used alone or in a mixture.

The base is used either alone or as a mixture of several bases, in an equimolar amount or in excess (1.0 to 2.5 equivalents, preferably 1.0 to 1.2 equivalents).

The oxidizing agent is also used in an equimolar amount or in excess (1 to 7 equivalents, preferably 2 to 3 equivalents).

The catalyst is used in an equimolar amount or in deficiency (0.0001 to 0.5 equivalent, preferably 0.001 to 0.01 equivalent).

The reactants can be added in one portion or in several portions over a period of up to 24 hours, preferably up to 6 hours, especially 0.05 to 6 hours. After addition of individual reactants, a continued stirring time (0.1 to 12 hours, preferably 0.5 to 3 hours) may be advantageous.

The reaction temperature of the oxidation is in the range from −20° C. to 60° C., preferably in the range from 10° C. to 40° C. The deprotonation of the reactant of the formula (2) can be performed at the same temperature as, or a different temperature than, the oxidation.

The reaction can optionally be performed under pressure.

For performance, it is advantageous when the N-sulfonyl-substituted 3-triazinyloxindole is first initially charged with the base (total amount or portion) in a suitable solvent, and then the catalyst and optionally a further amount of the same or another base or of a mixture of different bases is added in one or more portions, before the oxidizing agent is added.

One addition variant consists, in the case of use of potassium permanganate as an oxidizing agent in initially charging the oxidizing agent and the base in a suitable solvent and then adding the N-sulfonyl-substituted 3-triazinyloxindole, either in substance or dissolved or suspended in one of the solvents mentioned, in one or more portions. Alternatively, the base can also be added in one or more portions to the initially charged N-sulfonyl-substituted 3-triazinyloxindole and the oxidizing agent.

It is within the scope of the invention that the N-sulfonyl-substituted 3-triazinyloxindole is added to the reaction mixture as a salt. In this case, it is optionally possible to use less base.

The N-sulfonyl-substituted 3-triazinyloxindole and the base can be added to the reaction mixture either in pure form or premixed with one another, or dissolved or suspended in a solvent or a solvent mixture. It is possible that further solvent is added in the course of the reaction in order to enable better mixing of the reactants.

Depending on the reaction conditions used, the continued stirring time after addition of all reactants is in the range of up to 96 hours, preferably 0.05 to 24 hours.

The workup and isolation of the desired product of the formula (1) can be effected in various ways, and depends, for example, on the selection of the solvent or depends on whether the product is a solid or a liquid.

The reaction mixture which comprises a solid product of the formula (1) or (1-1) is filtered. The solid product thus obtained can be washed with suitable solvents and/or aqueous acids.

It is additionally envisaged that another, higher-boiling solvent in which the product is more sparingly soluble is added to the reaction mixture comprising product of the general formula (1-1), and the lower-boiling solvent is distilled off completely or partially. Subsequently, the product in solid form is filtered off and can be washed with suitable solvents and/or aqueous acids.

It is also within the scope of the invention that the product obtained after filtration and optional washing is extracted by stirring from a suitable solvent or a mixture of several solvents, in order to obtain the product in a higher purity.

Another means of workup consists in the extraction of the reaction mixture with a suitable solvent, from which the product is subsequently isolated.

The products of the formula (1-1) can be isolated either as free sulfonanilides (i.e. compounds protonated on the sulfonanilide nitrogen) or as salts (i.e. compounds deprotonated on the sulfonanilide nitrogen and having a cationic counterion). The salts may comprise potassium, sodium, cesium, lithium, barium or tetraalkylammonium as suitable cationic counterions.

It is likewise envisaged that the products of the formula (1-1) present in the reaction mixture, or the salts, can be converted further to conversion products without preceeding isolation.

More particularly, the products of the formula (1-1) present in the reaction mixture, or the salts, can be converted with or without isolation to give conversion products by alkylation on the sulfonanilide nitrogen to give N-alkyl-N-[2-(1,3,5-triazin-2-ylcarbonyl)phenyl]alkanesulfonamides.

The N-alkyl-N-[2-(1,3,5-triazin-2-ylcarbonyl)phenyl]alkanesulfonamides of the general formula (4-1) thus obtainable

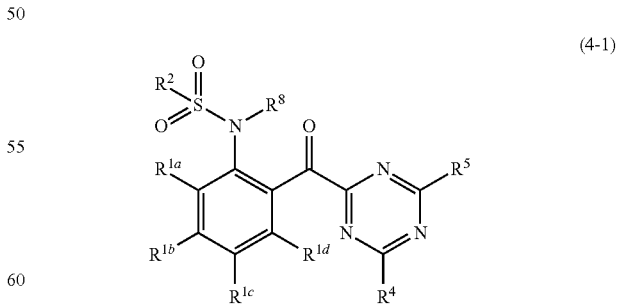

(4-1)

have been demonstrated to have herbicidal activity (WO 2007/031208 A2) and fungicidal activity (WO 2006/008159 A1).

Obtaining N-alkyl-N-[2-(1,3,5-triazin-2-ylcarbonyl)phenyl]alkanesulfonamides of the general formula (4-1) proceeding from N-sulfonyl-substituted 3-triazinyloxindoles of the formula (2-1) is economically advantageous compared to known synthesis routes.

The present invention therefore also provides for the use of N-sulfonyl-substituted 3-triazinyloxindoles of the formula (2-1)

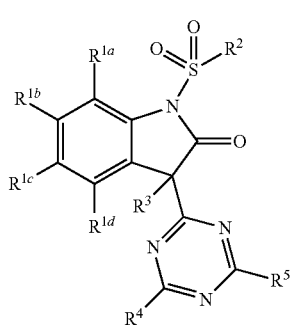

(2-1)

or salts thereof (2-1a)

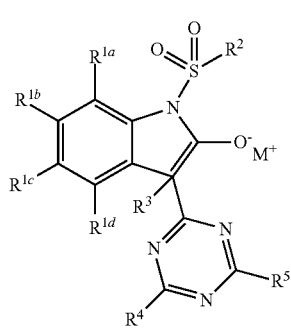

(2-1a)

in each of which $R^{1a}$ to $R^{1d}$ are each independently selected from the group consisting of hydrogen, fluorine, chlorine, bromine, iodine and from ($C_1$-$C_6$)-alkyl where the alkyl radical is branched or unbranched and is unsubstituted or substituted by one or more substituents selected from the group consisting of fluorine, chlorine, ($C_1$-$C_4$)-alkoxy and ($C_3$-$C_7$)-cycloalkyl, ($C_3$-$C_7$)-cycloalkyl where the cycloalkyl radical is unsubstituted or substituted by one or more substituents selected from the group consisting of fluorine, chlorine, ($C_1$-$C_4$)-alkyl and ($C_3$-$C_7$)-cycloalkyl and ($C_1$-$C_4$)-alkoxy, ($C_1$-$C_6$)-alkoxy where the alkoxy radical is branched or unbranched and is unsubstituted or substituted by one or more substituents selected from the group consisting of fluorine, chlorine, ($C_1$-$C_4$)-alkoxy and ($C_3$-$C_7$)-cycloalkyl, ($C_3$-$C_7$)-cycloalkoxy where the cycloalkoxy radical is unsubstituted or substituted by one or more substituents selected from the group consisting of fluorine, chlorine, ($C_1$-$C_4$)-alkyl and ($C_1$-$C_4$)-alkoxy, ($C_1$-$C_6$)-alkylthio where the alkylthio radical is branched or unbranched and is unsubstituted or substituted by one or more substituents selected from the group consisting of fluorine, chlorine, ($C_1$-$C_4$)-alkyl and ($C_1$-$C_4$)-alkoxy, ($C_3$-$C_7$)-cycloalkylthio where the cycloalkylthio radical is unsubstituted or substituted by one or more substituents selected from the group consisting of fluorine, chlorine, ($C_1$-$C_4$)-alkyl and ($C_1$-$C_4$)-alkoxy and phenyl or 1-naphthyl or 2-naphthyl or a five- or six-membered heteroaromatic ring having 1 to 2 heteroatoms, where the heteroatoms are each selected independently from the group consisting of O and N, and where the aryl or heteroaryl radical is unsubstituted or substituted by one or more substituents selected from the group consisting of fluorine, chlorine, bromine, iodine, ($C_1$-$C_4$)-alkyl, ($C_1$-$C_4$)-alkoxy and ($C_3$-$C_7$)-cycloalkyl and ($C_1$-$C_4$)-alkylthio, and $R^2$ is ($C_1$-$C_6$)-alkyl where the alkyl radical is unsubstituted or fully or partly substituted by fluorine, or ($C_3$-$C_7$)-cycloalkyl where the cycloalkyl radical is unsubstituted or fully or partly substituted by fluorine, $R^3$ is hydrogen, and $R^4$ and $R^5$ are each hydrogen, ($C_1$-$C_6$)-alkyl where the alkyl radical is unsubstituted or substituted by one or more substituents selected from the group consisting of fluorine, chlorine, ($C_1$-$C_4$)-alkoxy or ($C_3$-$C_7$)-cycloalkyl, ($C_1$-$C_6$)-alkoxy where the alkoxy radical is branched or unbranched and is unsubstituted or substituted by one or more substituents selected from the group consisting of fluorine, chlorine, ($C_1$-$C_4$)-alkoxy and ($C_3$-$C_7$)-cycloalkyl, wherein M in the salts of the general formula (2-1a) is Li, Na, K, Cs, Ba, Mg, Ca, Zn or $N(R^c)_4$ in which $R^c$=H or ($C_1$-$C_6$)-alkyl or benzyl, and where the number of counterions $M^+$ is guided by the particular charge, such that the compound of the general formula (2-1a) is uncharged overall, as reactants or as intermediates for the synthesis of active ingredients in the agricultural sector.

Particular preference is given to the use of N-sulfonyl-substituted 3-triazinyloxindoles of the formula (2-1) or salts of the formula (2-1a), where $R^{1a}$ to $R^{1d}$ are each independently selected from the group consisting of hydrogen, fluorine, chlorine, and from ($C_1$-$C_6$)-alkyl where the alkyl radical is branched or unbranched, ($C_1$-$C_6$)-alkoxy where the alkoxy radical is branched or unbranched, and $R^2$ is methyl, where the methyl is fully or partly substituted by fluorine, or ($C_3$-$C_7$)-cycloalkyl where the cycloalkyl radical is fully or partly substituted by fluorine, $R^3$ is hydrogen, and $R^4$ and $R^5$ are each independently ($C_1$-$C_4$)-alkyl where the alkyl radical is branched or unbranched, ($C_1$-$C_4$)-alkoxy where the alkoxy radical is branched or unbranched, where M in the salts of the general formula (2-1a) is Na and K, as intermediates for the synthesis of active ingredients in the agricultural sector.

Very particular preference is given to the use of N-sulfonyl-substituted 3-triazinyloxindoles of the formula (2-1) or salts of the formula (2-1a), where $R^{1a}$ to $R^{1d}$ are each independently selected from the group consisting of hydrogen, fluorine, chlorine, methoxy, and $R^2$ is difluoromethyl or trifluoromethyl, $R^3$ is hydrogen, and $R^4$ and $R^5$ are each independently methoxy, as intermediates for the synthesis of active ingredients in the agricultural sector.

Most preferred is the use of N-sulfonyl-substituted 3-triazinyloxindoles of the formula (2-1) or salts of the formula (2-1a), where $R^{1a}$ to $R^{1d}$ are each independently selected from the group consisting of hydrogen and fluorine, $R^2$ is difluoromethyl, $R^3$ is hydrogen, and $R^4$ and $R^5$ are each independently methoxy, as intermediates for the synthesis of active ingredients in the agricultural sector.

The above-described oxidation process for preparing compounds of the general formula (1-1) is characterized by the mechanism of oxidative ring opening, and is thus based on the selection of oxindoles as reactants, since these are amenable to oxidative ring opening.

The selection of compounds with oxindole structure as reactants, or intermediates, also characterizes a multistage process for preparing compounds of the general formula (1-1) and, proceeding therefrom, compounds of the general formula (4-1), which are known to be notable for herbicidal and fungicidal action.

The above-described oxidation process, which is based on the oxidative ring opening of oxindole compounds of the general formula (2-1), for preparing compounds of the general formula (1-1) is a component step of the multistage process described in scheme 7.

The oxindole compounds used as reactants, or intermediates, in the multistage process are summarized in scheme 7 below, and designated with the general formulae (7-1), (6-1), (5-1) and (2-1).

Scheme 7: Multistage process for preparing compounds of the general formula (1-1) and (4-1) which are suitable for crop protection and are especially herbicidal

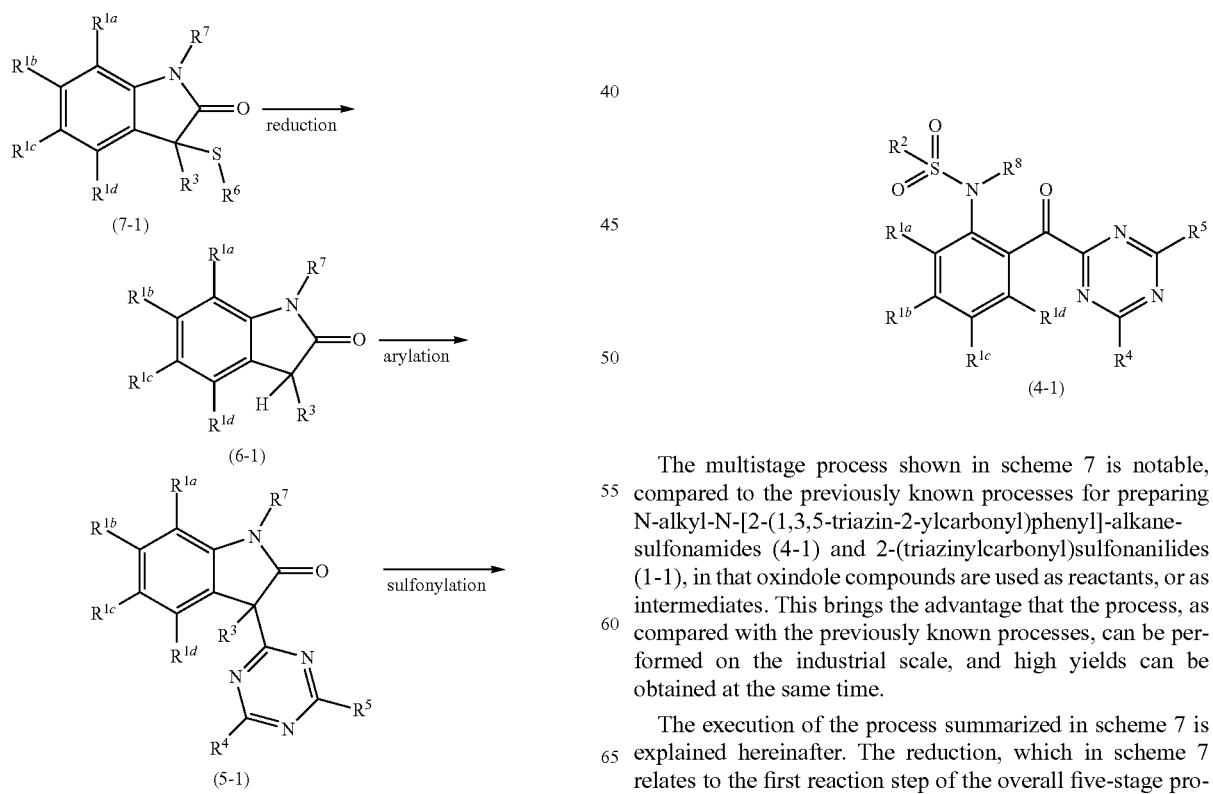

The multistage process shown in scheme 7 is notable, compared to the previously known processes for preparing N-alkyl-N-[2-(1,3,5-triazin-2-ylcarbonyl)phenyl]-alkanesulfonamides (4-1) and 2-(triazinylcarbonyl)sulfonanilides (1-1), in that oxindole compounds are used as reactants, or as intermediates. This brings the advantage that the process, as compared with the previously known processes, can be performed on the industrial scale, and high yields can be obtained at the same time.

The execution of the process summarized in scheme 7 is explained hereinafter. The reduction, which in scheme 7 relates to the first reaction step of the overall five-stage process, is treated here as an independent preliminary stage B).

The other reaction steps summarized in scheme 7, i.e. the steps of arylation, sulfonylation, oxidation and alkylation, are referred to collectively hereinafter as process A).

A) A process for preparing N-alkyl-N-[2-(1,3,5-triazin-2-ylcarbonyl)phenyl]alkanesulfonamides of the formula (4-1)

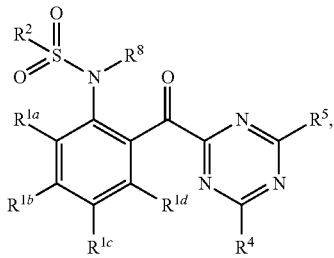

(4-1)

in which $R^{1a}$ to $R^{1d}$ are each independently selected from the group consisting of hydrogen, fluorine, chlorine, bromine, iodine and from ($C_1$-$C_6$)-alkyl where the alkyl radical is unsubstituted or substituted by one or more substituents selected from the group consisting of fluorine, chlorine, ($C_1$-$C_4$)-alkoxy and ($C_3$-$C_7$)-cycloalkyl, ($C_3$-$C_7$)-cycloalkyl where the cycloalkyl radical is unsubstituted or substituted by one or more substituents selected from the group consisting of fluorine, chlorine, ($C_1$-$C_4$)-alkyl and ($C_3$-$C_7$)-cycloalkyl and ($C_1$-$C_4$)-alkoxy, ($C_1$-$C_6$)-alkoxy where the alkoxy radical is unsubstituted or substituted by one or more substituents selected from the group consisting of fluorine, chlorine, ($C_1$-$C_4$)-alkoxy and ($C_3$-$C_7$)-cycloalkyl, ($C_3$-$C_7$)-cycloalkoxy where the cycloalkoxy radical is unsubstituted or substituted by one or more substituents selected from the group consisting of fluorine, chlorine, ($C_1$-$C_4$)-alkyl and ($C_1$-$C_4$)-alkoxy, ($C_1$-$C_6$)-alkylthio where the alkylthio radical is unsubstituted or substituted by one or more substituents selected from the group consisting of fluorine, chlorine, ($C_1$-$C_4$)-alkyl and ($C_1$-$C_4$)-alkoxy, ($C_3$-$C_7$)-cycloalkylthio where the cycloalkylthio radical is unsubstituted or substituted by one or more substituents selected from the group consisting of fluorine, chlorine, ($C_1$-$C_4$)-alkyl and ($C_1$-$C_4$)-alkoxy and phenyl or 1-naphthyl or 2-naphthyl or a five- or six-membered heteroaromatic ring having 1 to 2 heteroatoms, where the heteroatoms are each selected independently from the group consisting of O and N, and where the aryl or heteroaryl radical is unsubstituted or substituted by one or more substituents selected from the group consisting of fluorine, chlorine, bromine, iodine, ($C_1$-$C_4$)-alkyl, ($C_1$-$C_4$)-alkoxy and ($C_3$-$C_7$)-cycloalkyl and ($C_1$-$C_4$)-alkylthio, and $R^2$ is ($C_1$-$C_6$)-alkyl where the alkyl radical is unsubstituted or fully or partly substituted by fluorine, or ($C_3$-$C_7$)-cycloalkyl where the cycloalkyl radical is unsubstituted or fully or partly substituted by fluorine, $R^4$ and $R^5$ are each independently hydrogen, ($C_1$-$C_6$)-alkyl where the alkyl radical is unsubstituted or substituted by one or more substituents selected from the group consisting of fluorine, chlorine, ($C_1$-$C_4$)-alkoxy and ($C_3$-$C_7$)-cycloalkyl, ($C_1$-$C_6$)-alkoxy where the alkoxy radical is branched or unbranched and is unsubstituted or substituted by one or more substituents selected from the group consisting of fluorine, chlorine, ($C_1$-$C_4$)-alkoxy and ($C_3$-$C_7$)-cycloalkyl, and $R^8$ is ($C_1$-$C_6$)-alkyl where the alkyl radical is unsubstituted or partly or fully substituted by fluorine, ($C_1$-$C_6$)-cycloalkyl, ($C_1$-$C_6$)-alkenyl or ($C_1$-$C_6$)-alkoxyalkyl, where each of the radicals mentioned is unsubstituted or substituted partly or fully by fluorine, wherein a 1,3-dihydro-2H-indol-2-one of the formula (6-1)

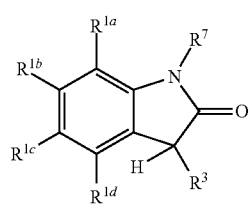

(6-1)

in which $R^{1a}$ to $R^{1d}$ are each as defined for formula (4-1), $R^3$ is hydrogen, and $R^7$ is hydrogen, is converted in a first step by arylation to give a triazinyl-substituted oxindole of the formula (5-1)

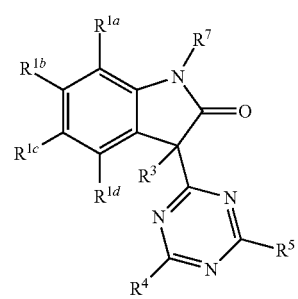

(5-1)

in which $R^{1a}$ to $R^{1d}$ and $R^4$ and $R^5$ are each as defined for the formula (4-1) and $R^3$ and $R^7$ are each as defined for the formula (6-1), and the arylation products of the formula (5-1) are converted in a second step by sulfonylation to give N-sulfonyl-substituted 3-triazinyloxindoles of the formula (2-1)

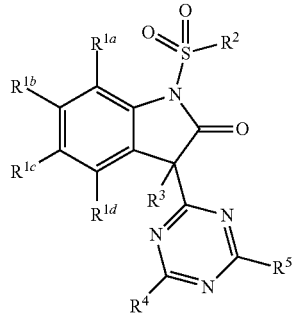

(2-1)

in which
R$^{1a}$ to R$^{1d}$, R$^2$ and R$^4$ and R$^5$ are each as defined in formula (4-1) and R$^3$ is as defined for formula (6-1),
and the sulfonylation products of the formula (2-1) are converted in a
third step by
oxidative ring opening to give a 2-(triazinylcarbonyl)sulfonanilide of the formula (1-1)

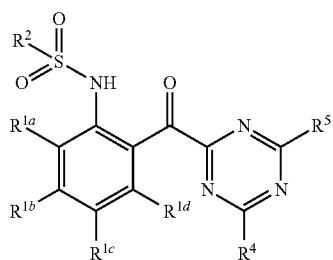

(1-1)

in which
R$^{1a}$ to R$^{1d}$, R$^2$ and R$^4$ and R$^5$ are each as defined for formula (4-1),
and the oxidation products of the formula (1-1) are converted in a
fourth step by
alkylation to give an N-alkyl-N-[2-(1,3,5-triazin-2-ylcarbonyl)phenyl]alkanesulfonamide of the formula (4-1)

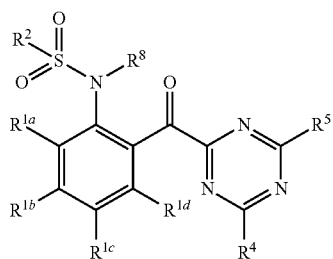

(4-1)

in which
R$^{1a}$ to R$^{1d}$, R$^2$, R$^4$, R$^5$ and R$^8$ are each as defined for formula (4-1),
wherein the alkylating reagent used is
X—R$^8$, where X is chlorine, bromine or iodine and R$^8$ is as defined above for formula (4-1), or
(R$^8$)$_2$SO$_4$, in which R$^8$ is as defined above for formula (4-1).

The process A) for preparing N-alkyl-N-[2-(1,3,5-triazin-2-ylcarbonyl) phenyl]alkanesulfonamides of the formula (4-1) consists of four component steps which, with the exception of the oxidation—the subject matter of the present invention—are the subject matter of prior applications:

Arylation of substituted or unsubstituted 1,3-dihydro-2H-indol-2-ones (6-1) to triazinyl-substituted oxindoles (5-1). This process is possible on the industrial scale and is described in patent application EP 10196205.8. With regard to the practicability of the arylation, reference is made here to the content of patent application EP 10196205.8.

Sulfonylation of triazinyl-substituted oxindoles (5-1) to N-sulfonyl-substituted 3-triazinyloxindoles (2-1). This process is possible on the industrial scale and is described in patent application EP 11159875.1. With regard to the practicability of the sulfonylation, reference is made here to the contents of patent application EP 11159875.1.

Oxidative ring opening of N-sulfonyl-substituted 3-triazinyloxindoles (2-1) to 2-(triazinylcarbonyl)sulfonanilides (1-1). This process is possible on the industrial scale and forms part of the subject matter of the present invention.

Alkylation of 2-(triazinylcarbonyl)sulfonanilides (1-1) to N-alkyl-N-[2-(1,3,5-triazin-2-ylcarbonyl)phenyl]alkanesulfonamides (4-1). This process is described in patent application WO 2006/008159 A1. With regard to the practicability of the alkylation, reference is made here to the contents of patent application WO 2006/008159 A1.

The arylation is performed in the presence
of a carbonate, or
of a hydroxide, or
of a phosphate, or
in a mixture comprising at least two of the aforementioned bases.

Preferably, in the arylation, the bases used are potassium carbonate, sodium carbonate, sodium hydroxide, potassium hydroxide, or an at least two-component mixture consisting of at least one of the two carbonates: potassium carbonate and sodium carbonate, and of at least one of the two hydroxides: potassium hydroxide and sodium hydroxide.

The sulfonylation is performed in the presence
of a 1-substituted imidazole base, or
of a base mixture comprising at least one 1-substituted imidazole base.

Particularly preferred imidazole bases for the performance of the sulfonylation are 1-methyl-1H-imidazole, 1-butyl-1H-imidazole or 1-benzyl-1H-imidazole, which can be used individually or in a mixture, very particular preference being given to the use of 1-methyl-1H-imidazole.

The alkylation can be effected with standard alkylating agents. In the case of a methylation, preference is given to using dimethyl sulfate.

The herbicidal action (see WO 2007/031208 A2) and fungicidal action (see WO 2006/008159 A1) of N-alkyl-N-[2-(1,3,5-triazin-2-ylcarbonyl)phenyl]alkanesulfonamides of the formula (4-1) has been known for a long time.

Thus, the above details regarding the practicability of the reactions combined in process A), consisting of arylation, sulfonylation, oxidation and alkylation, demonstrate the suitability of oxindoles of the formulae (6-1), (5-1), (2-1), and compounds of the formula (1-1), for preparation of crop protection agents of the formula (4-1).

B) The process for preparing N-alkyl-N-[2-(1,3,5-triazin-2-ylcarbonyl)phenyl]alkanesulfonamides of the formula (4-1), wherein the compounds of the formula (6-1) used as the reactant are prepared in a preceding process step in which conversion is effected proceeding from a 3-(alkylsulfanyl)-1,3-dihydro-2H-indol-2-one of the formula (7-1)

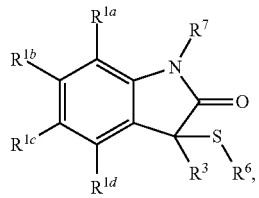

(7-1)

in which $R^{1a}$ to $R^{1d}$ are each as defined for formula (4-1), $R^3$ is hydrogen, $R^7$ is hydrogen, and $R^6$ is an unsubstituted or substituted $(C_1-C_{14})$-alkyl, $(C_3-C_7)$-cycloalkyl, benzyl or a $CH_2$—$C(O)O$—$(C_1-C_6)$-alkyl, by reduction to give a 1,3-dihydro-2H-indol-2-one (6-1)

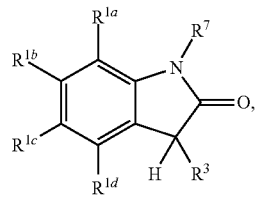

(6-1)

in which $R^{1a}$ to $R^{1d}$, $R^3$ and $R^7$ are each as defined for formula (7-1).

Process B) relates to the reduction of substituted or unsubstituted 3-(alkylsulfanyl)-1,3-dihydro-2H-indol-2-ones (7-1) to substituted or unsubstituted 1,3-dihydro-2H-indol-2-ones (6-1). This process is possible on the industrial scale and is described in patent application EP 10162381.7. With regard to the practicability of the reduction, reference is made here to the contents of patent application EP 10162381.7.

In the reduction, a) a compound of the formula (7-1) is dissolved or suspended in a polar solvent, b) a sulfur-containing salt is added to the solution or suspension, and c) the reaction mixture is heated under reflux at a temperature not exceeding the boiling temperature of the polar solvent.

Particularly preferred sulfur-containing salts are sodium salts selected from the group consisting of sodium bisulfite, sodium sulfite, sodium thionite, sodium dithionite and sodium thiosulfate.

The invention also provides the 2-(triazinylcarbonyl)sulfonanilides of the formula (1-1) prepared by the oxidation process explained above, i.e. the oxidative ring opening of oxindole compounds of the formula (2-1),

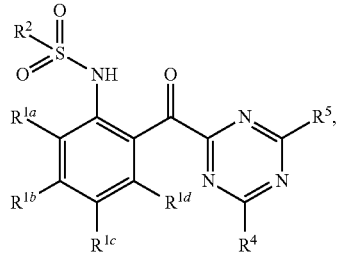

(1-1)

in which $R^{1a}$ to $R^{1d}$, $R^2$, $R^4$ and $R^5$ are each as defined for formula (4-1), i.e.

$R^{1a}$ to $R^{1d}$ are each independently selected from the group consisting of hydrogen, fluorine, chlorine, bromine, iodine and from $(C_1-C_6)$-alkyl where the alkyl radical is unsubstituted or substituted by one or more substituents selected from the group consisting of fluorine, chlorine, $(C_1-C_4)$-alkoxy and $(C_3-C_7)$-cycloalkyl, $(C_3-C_7)$-cycloalkyl where the cycloalkyl radical is unsubstituted or substituted by one or more substituents selected from the group consisting of fluorine, chlorine, $(C_1-C_4)$-alkyl and $(C_3-C_7)$-cycloalkyl and $(C_1-C_4)$-alkoxy, $(C_1-C_6)$-alkoxy where the alkoxy radical is unsubstituted or substituted by one or more substituents selected from the group consisting of fluorine, chlorine, $(C_1-C_4)$-alkoxy and $(C_3-C_7)$-cycloalkyl, $(C_3-C_7)$-cycloalkoxy where the cycloalkoxy radical is unsubstituted or substituted by one or more substituents selected from the group consisting of fluorine, chlorine, $(C_1-C_4)$-alkyl and $(C_1-C_4)$-alkoxy, $(C_1-C_6)$-alkylthio where the alkylthio radical is unsubstituted or substituted by one or more substituents selected from the group consisting of fluorine, chlorine, $(C_1-C_4)$-alkyl and $(C_1-C_4)$-alkoxy, $(C_3-C_7)$-cycloalkylthio where the cycloalkylthio radical is unsubstituted or substituted by one or more substituents selected from the group consisting of fluorine, chlorine, $(C_1-C_4)$-alkyl and $(C_1-C_4)$-alkoxy and phenyl or 1-naphthyl or 2-naphthyl or a five- or six-membered heteroaromatic ring having 1 to 2 heteroatoms, where the heteroatoms are each selected independently from the group consisting of O and N, and where the aryl or heteroaryl radical is unsubstituted or substituted by one or more substituents selected from the group consisting of fluorine, chlorine, bromine, iodine, $(C_1-C_4)$-alkyl, $(C_1-C_4)$-alkoxy and $(C_3-C_7)$-cycloalkyl and $(C_1-C_4)$-alkylthio, and $R^2$ is $(C_1-C_6)$-alkyl where the alkyl radical is unsubstituted or fully or partly substituted by fluorine, or $(C_3-C_7)$-cycloalkyl where the cycloalkyl radical is unsubstituted or fully or partly substituted by fluorine, $R^4$ and $R^5$ are each independently hydrogen, $(C_1-C_6)$-alkyl where the alkyl radical is unsubstituted or substituted by one or more substituents selected from the group consisting of fluorine, chlorine, $(C_1-C_4)$-alkoxy and $(C_3-C_7)$-cycloalkyl, $(C_1-C_6)$-alkoxy where the alkoxy radical is branched or unbranched and is unsubstituted or substituted by one or more substituents selected from the group consisting of fluorine, chlorine, ($C_1$-$C_4$)-alkoxy and ($C_3$-$C_7$)-cycloalkyl.

The aforementioned compounds of the formula (1-1) are important intermediates in the process explained above for preparation of herbicides or fungicides of the formula (4-1). The 2-(triazinylcarbonyl)sulfonanilides of the formula (1-1) prepared by oxidative ring opening of oxindole compounds of the formula (2-1) and subsequent alkylation likewise form part of the subject matter of the invention.

The examples which follow illustrate the invention in detail, but without limiting the subject matter thereof to these examples.

In the examples which follow, stated amounts are based on weight, unless specifically defined otherwise. In the description, the abbreviation % by wt.=percent by weight was used analogously therefor. For units of measurement, physical parameters and the like, customary abbreviations are used, for example h=hour(s), m.p.=melting point, l=liter, ml=milliliter, g=gram, min=minute(s), in vacuo=under reduced pressure, of theory=percent theoretical yield, RT=room temperature, eq.=equivalents.

The coupling patterns in the NMR spectra are described as they appear.

Proportions on the basis of HPLC analysis are, unless stated otherwise, reported in relative area percentages.

Percentages in the LC-MS analysis relate to the relative proportion of the particular component in the chromatogram.

Example 1

Preparation of N-{2-[(4,6-dimethoxy-1,3,5-triazin-2-yl)carbonyl]-6-fluorophenyl}-1,1-difluoromethanesulfonamide

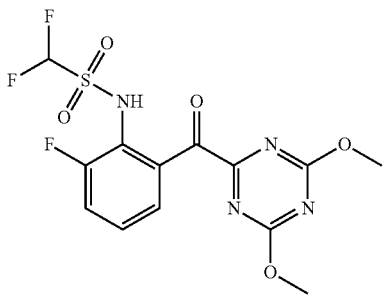 [SMILES: COc1nc(OC)nc(C(=O)c2cccc(F)c2NS(=O)(=O)C(F)F)n1]

Variant A (Oxidation with Hydrogen Peroxide and Iron Sulfate in Water/Acetonitrile): 1-[(Difluoromethyl)sulfonyl]-3-(4,6-dimethoxy-1,3,5-triazin-2-yl)-7-fluoro-1H-indol-2-ol (100 g) is initially charged in 330 ml of acetonitrile and the suspension is heated to 35° C. A solution of potassium hydrogencarbonate (25.4 g) in 145 ml of water is added dropwise within 45 min. Iron(II) sulfate heptahydrate (395 mg) and pyridine-2-carboxylic acid (175 mg) are premixed in 1 ml of water and added to the mixture. Hydrogen peroxide (35% in water, 58 g) is added dropwise over 135 min, and the internal temperature is kept at 25° C.-28° C. Stirring is continued for 170 min, sodium sulfite (3 g) and potassium hydrogencarbonate (3 g) is added, the mixture is concentrated to 282 g at 40° C. under reduced pressure, and the solid residue is filtered off. 2-Propanol (150 ml) is added to the solution and the pH is adjusted to 2 with hydrochloric acid, such that a solid precipitates out. After adding 160 ml of water, the solid is filtered off, washed with 100 ml of 2-propanol/water (1:4) and 200 ml of water, and dried. This gives N-{2-[(4,6-dimethoxy-1,3,5-triazin-2-yl)carbonyl]-6-fluorophenyl}-1,1-difluoromethanesulfonamide in a purity of 97% (86.2 g, 90% of theory).

LC-MS: M+H=393 (96%).

1H NMR (400 MHz, $CDCl_3$): δ (ppm)=9.2 (broad s, 1H), 7.54 (d, 1H), 7.47 (t, 1H), 7.34 (dt, 1H), 6.48 (t, 1H), 4.12 (s, 6H).

Variant B (Oxidation with Potassium Permanganate):

Potassium permanganate (184 mg) and potassium carbonate (96 mg) are initially charged in 2 ml of a mixture of water and acetonitrile (1:1) at 0° C. While cooling, 1-[(difluoromethyl)sulfonyl]-3-(4,6-dimethoxy-1,3,5-triazin-2-yl)-7-fluoro-1H-indol-2-ol (186 mg) is added as a solid in portions within 20 min, and the mixture is stirred for a further 90 min. For workup, dilute sulfuric acid (20% in water, 2 ml) is added, the mixture is stirred briefly until the end of gas evolution, and the mixture is added dropwise to a solution of sodium sulfite (10% in water, 3 ml). The organic solvent is substantially removed under reduced pressure and the aqueous residue is extracted with dichloromethane. The organic phase is washed once with a solution of ammonium chloride in water and concentrated. This gives N-{2-[(4,6-dimethoxy-1,3,5-triazin-2-yl)carbonyl]-6-fluorophenyl}-1,1-difluoromethanesulfonamide in an HPLC purity of >99% (123 mg, 72% of theory). The NMR corresponds to that of the product obtained in variant A.

Variant C (=Comparative Example 1C—Oxidation with Hydrogen Peroxide without Catalyst):

1-[(Difluoromethyl)sulfonyl]-3-(4,6-dimethoxy-1,3,5-triazin-2-yl)-7-fluoro-1H-indol-2-ol (60 g) is initially charged in 165 ml of acetonitrile and the suspension is heated to 35° C. A solution of potassium hydrogencarbonate (14.8 g) in 74 ml of water is added dropwise and the mixture is heated to 35° C. within 30 min and stirred at 35° C. for a further 10 min. The mixture is cooled again to 25° C. and hydrogen peroxide (35% in water, 34 g) is added dropwise within 4 hours, in the course of which the internal temperature is kept at 25° C.-27° C. The result is a clear homogeneous solution. The mixture is left to stand at 22° C. overnight. According to HPLC (210 nm, figures in area percent), 15% of the title compound and 78% alcohol (N-{2-[(4,6-dimethoxy-1,3,5-triazin-2-yl)(hydroxy)methyl]-6-fluorophenyl}-1,1-difluoromethanesulfonamide) have formed. Sodium sulfite (18 g) and then potassium hydrogencarbonate (19 g) are added to the mixture in portions, and the mixture is concentrated at 40° C. under reduced pressure, in the course of which 168 ml of distillate are removed. Since isolation of the product mixture as a filterable solid with 2-propanol is not possible as in example 1 variant A, the mixture is made up to a volume of 1 l with water and cooled to 5° C., the pH is adjusted to 2 with hydrochloric acid, and the precipitated solid is filtered off and washed with 1 l of water. This gives 50.1 g of a mixture which, according to HPLC, consists of the title compound (14% area) and the alcohol N-{2-[(4,6-dimethoxy-1,3,5-triazin-2-yl)(hydroxy)methyl]-6-fluorophenyl}-1,1-difluoromethanesulfonamide (82% area). The yield is 13% of theory (title compound) and 76% of theory (alcohol). The NMR of the mixture confirms the presence of title compound (approx. 12%) and alcohol (approx. 88%).

1H NMR (400 MHz, $CDCl_3$) of N-{2-[(4,6-dimethoxy-1,3,5-triazin-2-yl)(hydroxy)methyl]-6-fluorophenyl}-1,1-difluoromethanesulfonamide: δ (ppm)=9.4 (broad s, 1H), 7.48 (d, 1H), 7.31 (dt, 1H), 7.14 (t, 1H), 6.57 (t, 1H), 6.10 (s, 1H), 4.7 (broad s, 1H), 4.09 (s, 6H).

Synthesis examples 2 to 9 were performed by oxidation with hydrogen peroxide in acetonitrile/water in the presence of iron(II) sulfate heptahydrate and pyridine-2-carboxylic acid.

Example 2

N-{2-[(4,6-dimethoxy-1,3,5-triazin-2-yl)carbonyl]-4-methoxyphenyl}-1,1-difluoromethanesulfonamide

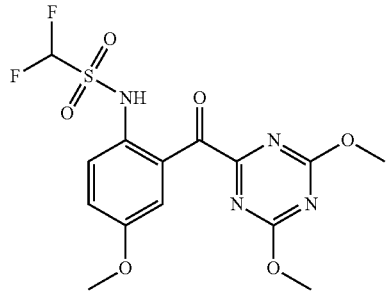 [SMILES: COc1ccc(NS(=O)(=O)C(F)F)c(C(=O)c2nc(OC)nc(OC)n2)c1]

LC-MS: M+H=405 (100%).

1H NMR (400 MHz, CDCl$_3$): δ (ppm)=10.5 (broad s, 1H), 7.78 (d, 1H), 7.19 (dd, 1H), 7.14 (d, 1H), 6.29 (t, 1H), 4.12 (s, 6H), 3.78 (s, 3H).

Example 3

N-{2-[(4,6-dimethoxy-1,3,5-triazin-2-yl)carbonyl]-4,6-difluorophenyl}-1,1-difluoromethanesulfonamide

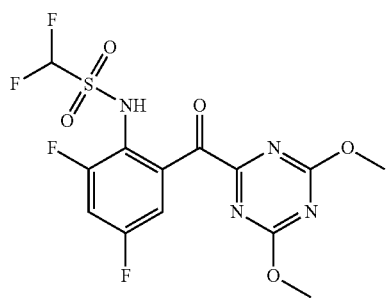 [SMILES: COc1nc(OC)nc(C(=O)c2cc(F)cc(F)c2NS(=O)(=O)C(F)F)n1]

LC-MS: M+H=411 (91%).

1H NMR (400 MHz, CDCl$_3$): δ (ppm)=8.2 (broad s, 1H), 7.35 (dd, 1H), 7.21 (dt, 1H), 6.35 (t, 1H), 4.12 (s, 6H).

Example 4

N-{2-[(4,6-dimethoxy-1,3,5-triazin-2-yl)carbonyl]-6-methoxyphenyl}-1,1-difluoromethanesulfonamide

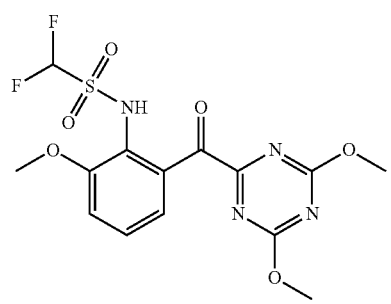 [SMILES: COc1nc(OC)nc(C(=O)c2cccc(OC)c2NS(=O)(=O)C(F)F)n1]

LC-MS: M+H=405 (98%).

1H NMR (400 MHz, CDCl$_3$): δ (ppm)=8.6 (broad s, 1H), 7.30-7.35 (m, 2H), 7.24 (dd, 1H), 6.52 (t, 1H), 4.11 (s, 6H), 3.96 (s, 3H).

Example 5

N-{2-[(4,6-diethoxy-1,3,5-triazin-2-yl)carbonyl]-6-fluorophenyl}-1,1-difluoromethanesulfonamide

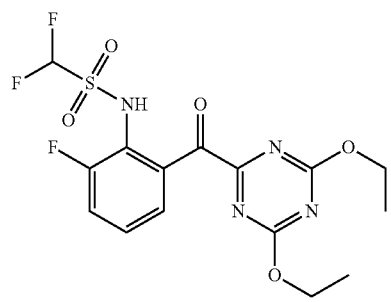 [SMILES: CCOc1nc(OCC)nc(C(=O)c2cccc(F)c2NS(=O)(=O)C(F)F)n1]

LC-MS: M−H=419 (100%).

1H NMR (600 MHz, CDCl₃): δ (ppm)=9.2 (broad s, 1H), 7.56 (d, 1H), 7.46 (t, 1H), 7.35 (dt, 1H), 6.50 (t, 1H), 4.55 (q, 4H), 1.46 (t, 6H).

Example 6

1,1-difluoro-N-{2-fluoro-6-[(4-methoxy-6-methyl-1,3,5-triazin-2-yl)carbonyl]phenyl}methanesulfonamide

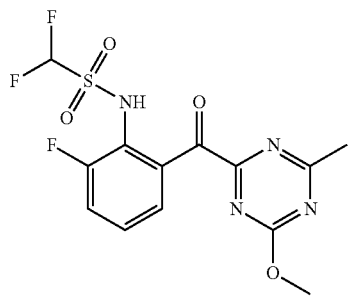 [SMILES: COc1nc(C)nc(C(=O)c2cccc(F)c2NS(=O)(=O)C(F)F)n1]

LC-MS: M+H=377 (100%).

1H NMR (600 MHz, CDCl₃): δ (ppm)=9.2 (broad s, 1H), 7.52 (d, 1H), 7.48 (t, 1H), 7.36 (dt, 1H), 6.50 (t, 1H), 4.11 (s, 3H), 2.72 (s, 3H).

Example 7

N-{2-[(4,6-dimethoxy-1,3,5-triazin-2-yl)carbonyl]-6-fluorophenyl}-1,1,1-trifluoromethanesulfonamide

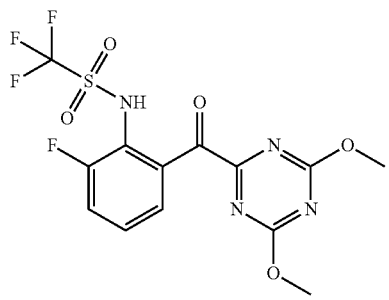 [SMILES: COc1nc(OC)nc(C(=O)c2cccc(F)c2NS(=O)(=O)C(F)(F)F)n1]

LC-MS: M+H=411 (88%).

1H NMR (400 MHz, CDCl₃): δ (ppm)=8.7 (broad s, 1H), 7.55 (dt, 1H), 7.40-7.50 (m, 2H), 4.12 (s, 6H).

Example 8

N-{2-chloro-6-[(4,6-dimethoxy-1,3,5-triazin-2-yl)carbonyl]phenyl}-1,1-difluoromethanesulfonamide

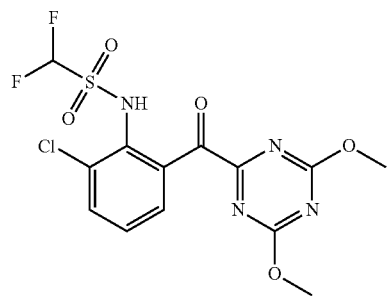 [SMILES: COc1nc(OC)nc(C(=O)c2cccc(Cl)c2NS(=O)(=O)C(F)F)n1]

LC-MS: M+H=409, 411 (100%).

1H NMR (400 MHz, DMSO-D₆): δ (ppm)=11.0 (broad s, 1H), 7.88 (dd, 1H), 7.75 (dd, 1H), 7.58 (t, 1H), 6.93 (t, 1H), 3.96 (s, 6H).

Synthesis examples 9 and 10 were performed by oxidation with potassium permanganate in acetonitrile/water.

Example 9

N-{2-[(4,6-dimethoxy-1,3,5-triazin-2-yl)carbonyl]-4-fluorophenyl}-1,1-difluoromethanesulfonamide

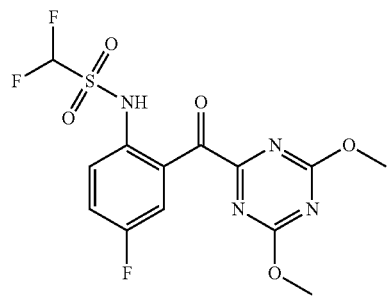 [SMILES: COc1nc(OC)nc(C(=O)c2cc(F)ccc2NS(=O)(=O)C(F)F)n1]

LC-MS: M+H=393 (96%).

1H NMR (400 MHz, CDCl$_3$): δ (ppm)=10.8 (broad s, 1H), 7.87 (dd, 1H), 7.34-7.42 (m, 2H), 6.33 (t, 1H), 4.13 (s, 6H).

Example 10

N-{2-[(4,6-dimethoxy-1,3,5-triazin-2-yl)carbonyl]phenyl}-1,1-difluoromethanesulfonamide

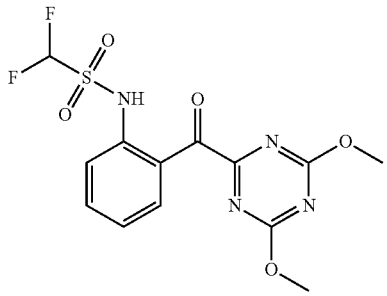 [SMILES: COc1nc(OC)nc(C(=O)c2ccccc2NS(=O)(=O)C(F)F)n1]

LC-MS: M+H=375 (90%).
1H NMR (400 MHz, CDCl$_3$): δ (ppm)=11.1 (broad s, 1H), 7.88 (d, 1H), 7.61-7.68 (m, 2H), 7.18 (t, 1H), 6.34 (t, 1H), 4.12 (s, 6H).

The invention claimed is:
1. A process for preparing a 2-(triazinylcarbonyl)sulfonanilides of formula (1-1)

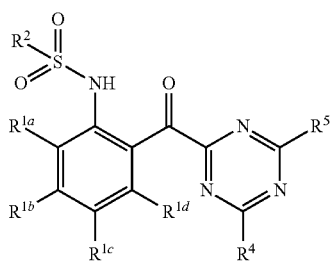

(1-1)

in which
R$^{1a}$ to R$^{1d}$ are each independently selected from the group consisting of
hydrogen, fluorine, chlorine, bromine, iodine and from
(C$_1$-C$_6$)-alkyl where the alkyl radical is branched or unbranched and is unsubstituted or substituted by at least one substituent selected from the group consisting of fluorine, chlorine, (C$_1$-C$_4$)-alkoxy and (C$_3$-C$_7$)-cycloalkyl,
(C$_3$-C$_7$)-cycloalkyl where the cycloalkyl radical is unsubstituted or substituted by at least one substituent selected from the group consisting of fluorine, chlorine, (C$_1$-C$_4$)-alkyl and (C$_3$-C$_7$)-cycloalkyl and (C$_1$-C$_4$)-alkoxy,
(C$_1$-C$_6$)-alkoxy where the alkoxy radical is branched or unbranched and is unsubstituted or substituted by at least one substituent selected from the group consisting of fluorine, chlorine, (C$_1$-C$_4$)-alkoxy and (C$_3$-C$_7$)-cycloalkyl,
(C$_3$-C$_7$)-cycloalkoxy where the cycloalkoxy radical is unsubstituted or substituted by at least one substituent selected from the group consisting of fluorine, chlorine, (C$_1$-C$_4$)-alkyl and (C$_1$-C$_4$)-alkoxy,
(C$_1$-C$_6$)-alkylthio where the alkylthio radical is branched or unbranched and is unsubstituted or substituted by at least one substituent selected from the group consisting of fluorine, chlorine, (C$_1$-C$_4$)-alkyl and (C$_1$-C$_4$)-alkoxy,
(C$_3$-C$_7$)-cycloalkylthio where the cycloalkylthio radical is unsubstituted or substituted by at least one substituent selected from the group consisting of fluorine, chlorine, (C$_1$-C$_4$)-alkyl and (C$_1$-C$_4$)-alkoxy, and
phenyl or 1-naphthyl or 2-naphthyl or a five- or six-membered heteroaromatic ring having from 1 to 2 heteroatoms, where the heteroatoms are each selected independently from the group consisting of O and N, and where the aryl or heteroaryl radical is unsubstituted or substituted by at least one substituent selected from the group consisting of fluorine, chlorine, bromine, iodine, (C$_1$-C$_4$)-alkyl, (C$_1$-C$_4$)-alkoxy and (C$_3$-C$_7$)-cycloalkyl and (C$_1$-C$_4$)-alkylthio, and
R$^2$ is
(C$_1$-C$_6$)-alkyl where the alkyl radical is unsubstituted or fully or partly substituted by fluorine, or
(C$_3$-C$_7$)-cycloalkyl where the cycloalkyl radical is unsubstituted or fully or partly substituted by fluorine, and
R$^4$ and R$^5$ are each hydrogen,
(C$_1$-C$_6$)-alkyl where the alkyl radical is unsubstituted or substituted by at least one substituent selected from fluorine, chlorine, (C$_1$-C$_4$)-alkoxy and (C$_3$-C$_7$)-cycloalkyl, or
(C$_1$-C$_6$)-alkoxy where the alkoxy radical is branched or unbranched and is unsubstituted or substituted by at least one substituent selected from the group consisting of fluorine, chlorine, (C$_1$-C$_4$)-alkoxy and (C$_3$-C$_7$)-cycloalkyl,
which comprises
using as a reactant an N-sulfonyl-substituted 3-triazinyloxindole of formula (2-1)

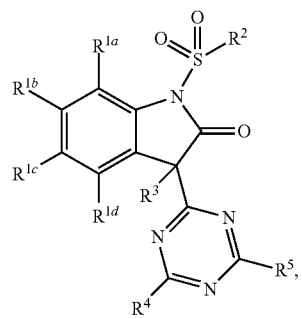

(2-1)

in which
R$^{1a}$ to R$^{1d}$ and R$^2$, R$^4$ and R$^5$ are each as defined in formula (1-1), and
R$^3$ is hydrogen
and
converting the reactant of formula (2-1) initially charged in a solvent in the presence
of a base and
of an oxidizing agent.
2. The process for preparing a 2-(triazinylcarbonyl)sulfonanilide of formula (1-1) as claimed in claim 1, where
R$^{1a}$ to R$^{1d}$ are each independently selected from the group consisting of hydrogen, fluorine, chlorine, bromine, iodine and from
(C$_1$-C$_6$)-alkyl where the alkyl radical is branched or unbranched and is unsubstituted or substituted by at least one substituent selected from the group consisting of fluorine, chlorine, ($C_1$-$C_4$)-alkoxy or ($C_3$-$C_7$)-cycloalkyl, ($C_3$-$C_7$)-cycloalkyl where the cycloalkyl radical is unsubstituted or substituted by at least one substituent selected from the group consisting of fluorine, chlorine, ($C_1$-$C_4$)-alkyl or ($C_3$-$C_7$)-cycloalkyl or ($C_1$-$C_4$)-alkoxy, ($C_1$-$C_6$)-alkoxy where the alkoxy radical is branched or unbranched and is unsubstituted or substituted by at least one substituent selected from the group consisting of fluorine, chlorine, ($C_1$-$C_4$)-alkoxy or ($C_3$-$C_7$)-cycloalkyl, ($C_3$-$C_7$)-cycloalkoxy where the cycloalkoxy radical is unsubstituted or substituted by at least one substituent selected from the group consisting of fluorine, chlorine, ($C_1$-$C_4$)-alkyl or ($C_1$-$C_4$)-alkoxy, and $R^2$ is ($C_1$-$C_6$)-alkyl where the alkyl radical is fully or partly substituted by fluorine, and $R^4$ and $R^5$ are each independently
($C_1$-$C_6$)-alkoxy where the alkoxy radical is branched or unbranched and is unsubstituted or substituted by at least one substituent selected from the group consisting of fluorine, chlorine, ($C_1$-$C_4$)-alkoxy or ($C_3$-$C_7$)-cycloalkyl.

3. The process for preparing a 2-(triazinylcarbonyl)sulfonanilide of formula (1-1) according to claim 1, where
$R^{1a}$ to $R^{1d}$ are each independently selected from the group consisting of hydrogen, fluorine, chlorine, methoxy, and
$R^2$ is difluoromethyl and $R^3$ is hydrogen, and
$R^4$ and $R^5$ are each methoxy.

4. The process for preparing a 2-(triazinylcarbonyl)sulfonanilide of formula (1-1) as claimed in claim 1, wherein the oxidizing agent is used in combination with a catalyst which has at least one heavy metal and/or a salt of a heavy metal as a constituent.

5. The process for preparing a 2-(triazinylcarbonyl)sulfonanilide of formula (1-1) as claimed in claim 4, wherein said oxidizing agent used is hydrogen peroxide in conjunction with a catalyst which comprises at least one heavy metal and/or a salt of a heavy metal as a constituent.

6. The process for preparing a 2-(triazinylcarbonyl)sulfonanilide of formula (1-1) as claimed in claim 4, wherein said oxidizing agent used is potassium permanganate without or with a catalyst which comprises at least one heavy metal and/or a salt of a heavy metal as a constituent.

7. The process for preparing a 2-(triazinylcarbonyl)sulfonanilide of formula (1-1) as claimed in claim 4, wherein the catalyst used comprises at least one of:
iron salts, iron powder, copper salts or copper powder, or a mixture thereof.

8. The process for preparing a 2-(triazinylcarbonyl)sulfonanilide of formula (1-1) as claimed in claim 4, wherein the catalyst used comprises:
at least one iron salt together with at least one complexing compound, or
at least one copper salt together with at least one complexing compound, or
a mixture thereof.

9. The process for preparing a 2-(triazinylcarbonyl)sulfonanilide of formula (1-1) as claimed in claim 7, wherein
said iron salt used comprises iron(II) sulfate and/or iron chloride, and
said copper salts used comprises copper(II) sulfate and/or copper(II) chloride.

10. The process for preparing a 2-(triazinylcarbonyl)sulfonanilide of formula (1-1) as claimed in claim 8, wherein said complexing compound used is pyridine-2-carboxylic acid.

11. The process for preparing a 2-(triazinylcarbonyl)sulfonanilide of formula (1-1) as claimed in claim 9, wherein the catalyst used is iron(II) sulfate together with pyridine-2-carboxylic acid.

12. The process for preparing a 2-(triazinylcarbonyl)sulfonanilide of formula (1-1) as claimed in claim 1, wherein the solvent used is a mixture comprising at least one water-miscible organic solvent and water.

13. The process for preparing a 2-(triazinylcarbonyl)sulfonanilide of formula (1-1) as claimed in claim 12, wherein said solvent used is acetonitrile and/or 2-propanol.

14. The process for preparing a 2-(triazinylcarbonyl)sulfonanilide of formula (1-1) as claimed in claim 1, wherein the base used is at least one of:
potassium carbonate, sodium carbonate or cesium carbonate,
potassium hydrogencarbonate or sodium hydrogencarbonate,
lithium hydroxide, sodium hydroxide, potassium hydroxide or barium hydroxide,
potassium phosphate ($K_3PO_4$), potassium hydrogenphosphate ($K_2HPO_4$) or sodium phosphate,
and/or
a mixture thereof.

15. The process for preparing a 2-(triazinylcarbonyl)sulfonanilide of formula (1-1) as claimed in claim 14, wherein said base used is potassium hydrogencarbonate or potassium carbonate or a mixture thereof.

* * * * *